US010375965B2

(12) United States Patent
Takanohashi et al.

(10) Patent No.: US 10,375,965 B2
(45) Date of Patent: Aug. 13, 2019

(54) PLANT DISEASE CONTROL COMPOSITION AND PLANT DISEASE CONTROL METHOD

(71) Applicant: SUMITOMO CHEMICAL COMPANY, LIMITED, Tokyo (JP)

(72) Inventors: Fumina Takanohashi, Tokyo (JP); Ayako Hirao, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/746,551

(22) PCT Filed: Jul. 27, 2016

(86) PCT No.: PCT/JP2016/072076
§ 371 (c)(1),
(2) Date: Jan. 22, 2018

(87) PCT Pub. No.: WO2017/018467
PCT Pub. Date: Feb. 2, 2017

(65) Prior Publication Data
US 2018/0213795 A1   Aug. 2, 2018

(30) Foreign Application Priority Data

Jul. 27, 2015   (JP) ................. 2015-147706
Dec. 22, 2015   (JP) ................. 2015-250264

(51) Int. Cl.
| | |
|---|---|
| *A01N 25/00* | (2006.01) |
| *A01N 37/46* | (2006.01) |
| *A01N 43/36* | (2006.01) |
| *A01N 43/78* | (2006.01) |
| *A01N 57/14* | (2006.01) |
| *A01N 63/00* | (2006.01) |
| *A01C 1/08* | (2006.01) |
| *A01N 43/56* | (2006.01) |
| *C12R 1/07* | (2006.01) |
| *C12N 1/20* | (2006.01) |

(52) U.S. Cl.
CPC ............ *A01N 63/00* (2013.01); *A01C 1/08* (2013.01); *A01N 25/00* (2013.01); *A01N 37/46* (2013.01); *A01N 43/36* (2013.01); *A01N 43/56* (2013.01); *A01N 43/78* (2013.01); *A01N 57/14* (2013.01); *C12N 1/20* (2013.01); *C12R 1/07* (2013.01)

(58) Field of Classification Search
CPC combination set(s) only.
See application file for complete search history.

(56) References Cited

U.S. PATENT DOCUMENTS

| | | |
|---|---|---|
| 6,995,007 B2 | 2/2006 | Gunner et al. |
| 7,666,406 B2 | 2/2010 | Gunner et al. |
| 2011/0110906 A1 | 5/2011 | Andersch et al. |
| 2015/0282483 A1* | 10/2015 | Sawada ............... A01N 43/56 504/100 |
| 2017/0188584 A1* | 7/2017 | Jabs .................... A01N 63/02 |

FOREIGN PATENT DOCUMENTS

| | | |
|---|---|---|
| JP | 10-109913 A | 4/1998 |
| JP | 2006-347885 A | 12/2006 |
| JP | 2011-519824 A | 7/2011 |
| JP | 2014-139223 A | 7/2014 |
| JP | 2015-504905 A | 2/2015 |
| JP | 2015-519352 A | 7/2015 |
| JP | 2016-155862 A | 9/2016 |
| WO | WO 03/055303 A1 | 7/2003 |
| WO | WO 2009/037242 A2 | 3/2009 |
| WO | WO 2011/162397 A1 | 12/2011 |
| WO | WO 2013/110591 A1 | 8/2013 |
| WO | WO 2013/178661 A1 | 12/2013 |
| WO | WO 2014/083033 A1 | 6/2014 |
| WO | WO 2015/004260 A1 | 1/2015 |

OTHER PUBLICATIONS

HCAPLUS abstract 2003:175116 (2003).*
HCAPLUS abstract 1995:964052 (1995).*
Derwent abstract 2007-050901; abstracting JP 2006-347885 (Dec. 2006).*
International Preliminary Report on Patentability and English translation of the Written Opinion of the International Searching Authority (PCT/IB/373 and PCT/ISA/237) for International Application No. PCT/JP2016/072072, dated Jan. 30, 2018.
International Preliminary Report on Patentability and English translation of the Written Opinion of the International Searching Authority (PCT/IB/373 and PCT/ISA/237) for International Application No. PCT/JP2016/072075, dated Jan. 30, 2018.
International Search Report (PCT/ISA/210) for International Application No. PCT/JP2016/072072, dated Sep. 13, 2016.
International Search Report (PCT/ISA/210) for International Application No. PCT/JP2016/072075, dated Sep. 13, 2016.
Peachey et al., "Mesiterpro Crop Protection Handbook," 2014 Centennial Edition, 2014, pp. 9, 191, 318-319, 358-360, 568-569.
The Insecticide Resistance Action Committee, "Mode of Action Classification," Insecticide Resistance Management, Fourth Edition, Dec. 2014, pp. 7, 20 (4 pages total).
International Preliminary Report on Patentability and English translation of the Written Opinion of the International Searching Authority (PCT/IB/373 and PCT/ISA/237) for International Application No. PCT/JP2016/072073, dated Jan. 30, 2018.
International Preliminary Report on Patentability and English translation of the Written Opinion of the International Searching Authority (PCT/IB/373 and PCT/ISA/237) for International Application No. PCT/JP2016/072074, dated Jan. 30, 2018.

(Continued)

*Primary Examiner* — John Pak
(74) *Attorney, Agent, or Firm* — Birch, Stewart, Kolasch & Birch, LLP

(57) ABSTRACT

The present invention, which addresses the problem of providing a composition that has an excellent effect of controlling plant disease, provides a plant disease control composition that includes the *Bacillus* strain APM-1 (New strain of *Bacillus*, APM-1) which is deposited under ATCC Accession No. PTA-4838 and at least one compound selected from the group consisting of ethaboxam, tolclofos-methyl, metalaxyl, fludioxonil, and a carboxamide compound represented by formula (1).

4 Claims, No Drawings

(56) References Cited

OTHER PUBLICATIONS

International Preliminary Report on Patentability and English translation of the Written Opinion of the International Searching Authority (PCT/IB/373 and PCT/ISA/237) for International Application No. PCT/JP2016/072076, dated Jan. 30, 2018.
International Search Report (PCT/ISA/210) for International Application No. PCT/JP2016/072073, dated Sep. 13, 2016.
International Search Report (PCT/ISA/210) for International Application No. PCT/JP2016/072074, dated Sep. 13, 2016.
International Search Report (PCT/ISA/210) for International Application No. PCT/JP2016/072076, dated Sep. 13, 2016.

MacBean (Ed.), "The Pesticide Manual," A World Compendium, Sixteenth Edition, BCPC, 2012, pp. 97, 117-118, 122-123, 528-529, 559-560, 577, 671-672, 863-865, 868-869, 1021-1022, 1216 (27 pages total).
U.S. Office Action for U.S. Appl. No. 15/747,513, dated Oct. 1, 2018.
U.S. Office Action for U.S. Appl. No. 15/747,699, dated Oct. 2, 2018.
Bartlett et al., "The Strobilurin Fungicides," Pest Management Science, vol. 58, 2002, pp. 649-662.
Epa, "Pesticide Fact Sheet: Ipconazole," Sep. 2004, pp. 1-17.
Miura, "Disinfectant/Microbicide Composition for Preventing Plant Diseases in Agriculture or Horticulture, Contains Spores of Bacteria Belonging to Bacillus Blended with Sterlized Agriculture/Horticulture Compound," Derwent-Acc-No. 2007-050901, Derwent-Week: 201151, Dec. 2006 2 pages.

* cited by examiner

PLANT DISEASE CONTROL COMPOSITION AND PLANT DISEASE CONTROL METHOD

TECHNICAL FIELD

The present invention relates to a composition for controlling plant diseases and a method for controlling plant diseases.

BACKGROUND ART

New strain of *Bacillus*, APM-1 (deposited under ATCC Accession No. PTA-4838), has been known as an active ingredient of compositions for controlling plant diseases and disclosed, for example, in Patent Document 1. Also, ethaboxam, tolclofos-methyl, metalaxyl, fludioxonil, as well as a carboxamide compound represented by the formula (1) (hereinafter referred to "the carboxamide compound (1)"):

[Chemical Formula 1]

(1)

were known as an active ingredient of compositions for controlling plant diseases and disclosed, for example, in Non-Patent Document 1 and Patent Document 2. There is need for a material which is still more effective for controlling plant diseases.

PRIOR ART DOCUMENTS

Patent Documents

Patent Document 1: WO 2003/055303
Patent Document 2: WO 2011/162397

Non-Patent Document

Non-Patent Document 1: The Pesticide Manual-16th edition (BCPC, ISBN: 978-1-901396-86-7)

DISCLOSURE OF THE INVENTION

Problems to be Solved by the Invention

Damage from plant disease is a cause of considerable loss of crop production, and there is a need to control such plant disease more effectively. Thus, it is an object of the present invention to provide a composition having an excellent controlling effect against plant diseases.

Means for Solving the Problems

The present inventors intensively studied to achieve the above object and have found that a composition comprising *Bacillus* strain APM-1 which has been deposited under ATCC Accession No. PTA-4838 (New strain of *Bacillus*, APM-1) and one or more compounds selected from the group consisting of ethaboxam, tolclofos-methyl, metalaxyl, fludioxonil and the carboxamide compound (1) has an excellent controlling effect against plant diseases.

Thus, the present invention includes the following [1] to [6].

[1] A composition for control plant diseases comprising *Bacillus* strain APM-1 (New strain of *Bacillus*, APM-1) deposited under ATCC Accession No. PTA-4838 and one or more compounds selected from the group consisting of ethaboxam, tolclofos-methyl, metalaxyl, fludioxonil and a carboxamide compound of the formula (1):

[Chemical Formula 2]

(1)

[2] The composition according to [1] comprising one or more compounds selected from the group consisting of ethaboxam, tolclofos-methyl, metalaxyl, fludioxonil and a carboxamide compound of the formula (1):

[Chemical Formula 3]

(1)

in an amount of $10^{-10}$ to $1.5 \times 10^7$ g per $10^{10}$ cfu of *Bacillus* APM-1.

[3] A plant seed or a vegetative propagation organ comprising *Bacillus* strain APM-1 (New strain of *Bacillus*, APM-1) deposited under ATCC Accession No. PTA-4838 and one or more compounds selected from the group consisting of ethaboxam, tolclofos-methyl, metalaxyl, fludioxonil and a carboxamide compound of the formula (1):

[Chemical Formula 4]

(1)

[4] The plant seed or vegetative propagation organ according to [3] comprising $10^4$ to $10^{14}$ cfu of *Bacillus* strain APM-1 and 0.000001 to 15 g of one or more compounds selected from the group consisting of ethaboxam, tolclofos-methyl, metalaxyl, fludioxonil and a carboxamide compound of the formula (1):

[Chemical Formula 5]

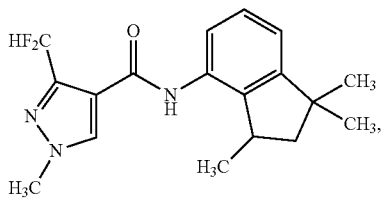

(1)

per 1 kg of the seed or vegetative propagation organ.

[5] A method for controlling plant diseases, comprising a step of applying *Bacillus* strain APM-1 (New strain of *Bacillus*, APM-1) deposited under ATCC Accession No. PTA-4838 and one or more compounds selected from the group consisting of ethaboxam, tolclofos-methyl, metalaxyl, fludioxonil and a carboxamide compound of the formula (1):

[Chemical Formula 6]

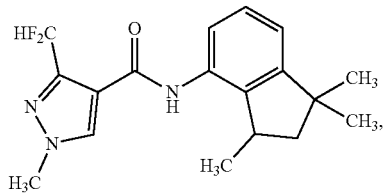

(1)

to a plant or a plant cultivation site.

[6] The method for controlling plant diseases according to [5] wherein the plant is a genetically modified plant.

Effect of Invention

The present invention provides an excellent composition for protecting seeds or vegetative propagation organs and plants grown therefrom from plant diseases.

DESCRIPTION OF EMBODIMENTS

The composition for controlling plant diseases of the present invention (hereinafter referred to as "the present composition") contains *Bacillus* strain APM-1 (New strain of *Bacillus*, APM-1) deposited under ATCC Accession No. PTA-4838 (hereinafter referred to "the present bacterial strain") and one or more compounds selected from the group consisting of ethaboxam, tolclofos-methyl, metalaxyl, fludioxonil and the carboxamide compound (1) (hereinafter referred to as "the present compound").

The present bacterial strain has been disclosed in WO 2003/055303 and deposited under the name "New strain of *Bacillus*, APM-1" under ATCC Accession No. PTA-4838 at ATCC (American Type Culture Collection). WO 2003/055303 describes that the strain is most similar to *Bucillus amyloliquefaciens*. The present bacterial strain is available from ATCC and can be cultured by a known procedure. The culture may be used as it is or may be separated and concentrated using a conventional industrial technique, such as, not limited to, membrane separation, centrifugal separation, or filtration separation. The fraction of the present bacterial strain thus obtained may be used directly as it contains certain water in the present composition, or if necessary, a dried product obtained by a dry method, such as freeze-dry or spray drying, may be used as the present bacterial strain.

In the present composition for controlling plant diseases, the present compound to be used in combination with the present bacterial strain is one or more selected from the groups consisting of ethaboxam, tolclofos-methyl, metalaxyl, fludioxonil and the carboxamide compound (1).

Ethaboxam is a known compound and has been described, e.g., on page 426 in "The Pesticide Manual-16th edition (Published by BCPC): ISBN 978-1-901396-36-7". Ethaboxam can be obtained from a commercially available formulation or produced by a known method.

Tolclofos-methyl is a known compound and has been described, e.g., on page 1125 in "The Pesticide Manual-16th edition (Published by BCPC): ISBN 978-1-901396-36-7". Tolclofos-methyl can be obtained from a commercially available formulation or produced by a known method.

Metalaxyl is a known compound and has been described, e.g., on page 733 in "The Pesticide Manual-16th edition (Published by BCPC): ISBN 978-1-901396-36-7". Tolclofos-methyl can be obtained from a commercially available formulation or produced by a known method.

Fludioxonil is a known compound and has been described, e.g., on page 512 in "The Pesticide Manual-16th edition (Published by BCPC): ISBN 978-1-901396-36-7". Tolclofos-methyl can be obtained from a commercially available formulation or produced by a known method.

The carboxamide compound (1) is a known compound and has been described, e.g., in the Patent Document 2. The carboxamide compound may be racemate or enantiomer, or a mixture of optional ratios of R-enantiomer and S-enantiomer and can be prepared by a known method.

The present composition can be prepared typically by mixing the present bacterial strain and the present compound, respectively, with a solid carrier or a liquid carrier, with addition of a surfactant or other auxiliary agents for formulation if necessary, followed by combining the present bacterial strain formulation and the compound formulation thus obtained. Alternatively, the present composition can be prepared by mixing the present bacterial strain with the present compound in advance, adding a solid carrier or a liquid carrier, with addition of a surfactant or other auxiliary agents for formulation if necessary, followed by formulating into a single formulation.

Examples of the solid carrier include mineral fine powders, such as kaolin clay, pyrophyllite clay, bentonite, montmorillonite, diatomaceous earth, synthetic hydrous silicon oxide, acidic clay, talc, clay, ceramic, quartz, sericite, vermiculite, pearlite, Oya stone, anthracite, limestone, coalite, and zeolite, inorganic compounds, such as sodium chloride, carbonate, sulfate, nitrate, and urea, organic fine powders, such as rice hulls, bran, wheat flour, and peat moss. Examples of the liquid carrier include water, vegetable oil, animal oil, and mineral oil. Examples of the auxiliary substance for formulation include anti-freezing agents, such as ethylene glycol, and propylene glycol, and thickening agents, such as carboxymethyl cellulose, and xanthan gum.

The present composition may contain the present bacterial strain in an effective amount, for example, at least $10^4$ cfu/g, typically $10^4$ to $10^{13}$ cfu/g, and preferably $10^7$ to $10^{12}$ cfu/g of the present composition.

The present composition may contain the present compound in an effective amount, for example, typically 0.0001 to 0.90 g, preferably 0.001 to 0.80 g, per 1 g of the present composition.

The present composition typically contains $10^{-10}$ to $1.5 \times 10^7$ g, preferably $10^{-7}$ to $10^5$ g, more preferably $10^{-5}$ to $10^2$ g of the present compound per $10^{10}$ cfu of the present bacterial strain.

The term "effective amount" as used herein refers to an amount of the present bacterial strain and the present compound that is able to exert the controlling effect against plant diseases.

The method of the invention for controlling plant diseases (hereinafter referred to as "the present controlling method") comprises a step of applying the present bacterial strain and one or more of the present compounds to a plant or a plant cultivation site.

In the present controlling method, the present bacterial strain and the present compound to be used are typically those which have been formulated and may be applied as separate formulations or as a present composition. The separate formulations may be applied simultaneously or independently.

In the present controlling method, the present bacterial strain and the present compound are applied in an effective amount.

In the present invention, examples of the cultivation site of the plant include paddy field, cultivated field, tea field, fruit orchard, non-agricultural land, seedling tray and nursery box, nursery soil and nursery mat, water culture medium in hydroponic farm, and the like. The plant disease may have already or not yet occurred in a cultivation site of plant or a place of disease occurrence.

In the present controlling method, examples of the method for treating the present bacterial strain and the present compound include foliage treatment, soil treatment, root treatment, seed treatment and vegetative propagation organ treatment.

Examples of the foliage treatment include treatment of the surface of the cultivated plant with spraying onto the foliage and stem.

Examples of the root treatment include immersing whole plant or a root of the plant in a solution containing the present bacterial strain and the present compound, as well as attaching a solid preparation containing the present bacterial strain, the present compound and a solid carrier to a root of the plant.

Examples of the soil treatment include soil broadcast, soil incorporation and chemical irrigation to soil.

Examples of the seed treatment and vegetative propagation organ treatment include applying seed treatment or vegetative propagation treatment using the present composition, specifically, such as spray treatment wherein a suspension of the present composition is sprayed onto the surface of the seed or the vegetative propagation organ, wet powder coating treatment wherein the present composition in a form of wettable powder is coated onto moist seed or vegetative propagation organ, smearing treatment wherein a liquid of the present composition prepared from wettable powder, emulsifiable concentrate or flowable formulation of the present composition, with addition of water if necessary, is applied onto seed or vegetative propagation organ, immersion treatment wherein seeds or vegetative propagation organs are immersed in a liquid containing the present composition for a certain period of time, and film coating treatment and pellet coating treatment of seeds with the present composition.

In the present invention, the simply described "plant" encompasses in its meaning "a seed of the plant" and "a vegetative propagation organ of the plant".

The term "vegetative propagation organ" as used herein means a part of root, stem, leaf or the like of the plant having the ability to grow when it is separated from the body and placed on soil, such as flower bulb, potato tuberous root, stem tuber, scaly bulb, corm, rhizophore, and strawberry runner.

In the present controlling method, the amount of the present bacterial strain and the present compound in the treatment varies depending on the kind of plant to be treated, the kind of plant disease to be targeted, and the occurrence frequency, the formulation form, the treatment period, the treatment method, the place to be treated, the weather condition or the like, and when a stem and a leaf of the plant or a soil where the plant grows is treated, the amount of the present bacterial strain for the treatment is usually $10^5$ to $10^{19}$ cfu, preferably $10^7$ to $10^{17}$ cfu, per 1 ha, and the amount of the present compound for the treatment is usually 10 to 5000 g, preferably 20 to 2000 g, per 1 ha. The composition in a form of wettable powder, water dispersible granules or the like may be used by diluting with water so that the concentration of the present bacterial strain is usually $10^3$ to $10^{12}$ cfu/L and that the concentration of the present compound is usually 0.0005 to 1% by weight. The composition in a form of dustable powder or granules may be used as it is.

In the seed treatment or vegetative propagation organ treatment, the amount of the present bacterial strain is usually $10^4$ to $10^{14}$ cfu, preferably $10^6$ to $10^{13}$ cfu per 1 kg of the seed or vegetative propagation organ, and the amount of the present compound is usually 0.000001 to 15 g, preferably 0.0001 to 10 g, per 1 kg of the of seed or vegetative propagation organ.

The weight of the seed or vegetative propagation organ means the weight thereof when treating with the present bacterial strain and the present compound or other agricultural chemicals before seeding or burying of the same.

By treating the seed or vegetative propagation organ as described above, a seed or vegetative propagation organ comprising the present bacterial strain and one or more compounds of the invention can be obtained. An adjuvant may be admixed if necessary during the seed treatment or vegetative propagation organs treatment.

Examples of the plant to which the present invention is applicable include the followings.

Agricultural crops: cereal crops, such as corn, wheat, barley, rye, oat, sorghum; pseudocereals, such as buckwheat; pulses, such as soybean, peanut; cotton; sugar beet; rice; oilseed rape; sunflower; sugar cane; tobacco; hop.

Vegetables: solanaceous crops (eggplant, tomato, potato, chili pepper, green pepper, etc.), cucurbitaceae crops (cucumber, pumpkin, zucchini, watermelon, melon, orienta melon, etc.), cruciferous vegetables (radish, turnip, horseradish, kohlrabi, chinese cabbage, cabbage, mustard, broccoli, cauliflower, etc.), asteraceae vegetables (burdock, garland *chrysanthemum*, artichoke, lettuce, etc.), liliaceae vegetables (green onion, onion, garlic, asparagus, etc.), umbelliferae vegetables (carrot, parsley, celery, parsnip, etc.), chenopodiaceae vegetables (spinach, chard, etc.), labiatae vegetables (*perilla*, mint, basil, etc.), leguminous crops (pea, kidney bean, adzuki bean, broad bean, chickpea, etc.), strawberry, sweet potato, yam, taro, konjac, ginger, okra.

Fruit trees: pome fruits (apple, Japanese pear, common pear, Chinese quince, quince, etc.), stone fruits (peach, plum, nectarine, Japanese plum, cherry, apricot, prune, etc.), citrus fruits (Satsuma mandarin, orange, lemon, lime, grapefruit, etc.), nuts (chestnut, walnut, hazel nut, almond, pistachio, cashew nut, macadamia nut, etc.), berries (blueberry, cranberry, blackberry, raspberry, etc.), grape, Japanese persimmon, olive, loquat, banana, coffee, date palm, coconut palm, oil palm.

Trees other than fruit trees: tea, mulberry, flowering trees (azalea, camellia, hydrangea, sasanqua, Japanese star anise, cherry, tulip tree, crape myrtle, orange osmanthus, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse chestnut, etc.), coral tree, podocarpus, cedar, Japanese cypress, croton, Japanese spindle tree, Japanese photinia.

Grasses: zoysia (zoysiagrass, Zoysia matrella, etc.), bermuda grasses (Cynodon dactylon, etc.), bent grasses (Agrostis alba, creeping bent grass, hiland bent, etc.), blueglasses (meadow grass, bird grass, etc.), fescue (tall fescue, chewings fescue, creeping red fescue, etc.), ryegrasses (darnel, rye grass, etc.), orchard grass, timothy grass.

Others: flowers (rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia, etc.), bio-fuel plants (Jatropha, safflower, camelina, switchgrass, Miscanthus, reed canary grass, giant reed, kenaf, cassava, willow, etc.), ornamental plants.

The present invention is preferably applied to cereal crops or millets. The present invention is more preferably applied to corn, wheat, sorghum, and soybean.

In the present invention, the variety of plant is not limited so long as it is commonly cultivated. The plants of such varieties include plants which have been conferred with one or more useful trait by a classical breeding technique or a genetic engineering technique (genetically modified plant) as well as stack varieties obtained by crossing such genetically modified plants.

Such useful characters include tolerance to herbicide, resistance to plant disease, disease resistance, stress tolerance, and improved quality of crops such as modified fatty acid residue composition of oils and fats.

Examples of the genetically modified plant include those listed in the genetically modified crop registration database (GM APPROVAL DATABASE) in the electronic information site (http://www.isaaa.org/) of the INTERNATINAL SERVICE for the ACQUISITION of AGRI-BIOTECH APPLICATIONS (ISAAA). More specifically, the plant may be a plant which has been conferred with an environmental stress tolerance, a disease resistance, a herbicide tolerance, a pest resistance or the like, or a plant wherein its trait has been modified with respect to growth and yield, quality of product, sterility or the like, by genetic recombination technology.

Examples of the plant conferred with a herbicide tolerance by gene recombination technology include genetically modified plants conferred with a tolerance to protoporphyrinogen oxidase (herein after referred to as PPO) herbicides such as flumioxazin; 4-hydroxyphenyl pyruvic acid dioxygenase (hereinafter abbreviated as HPPD) inhibitors such as isoxaflutole, mesotrione; acetolactate synthase (hereinafter referred to as ALS) inhibitors such as imazethapyr, thifensulfuron methyl; 5-enolpyruvylshikimate-3-phosphate synthase (hereinafter referred to as EPSP) inhibitors such as glyphosate; glutamine synthetase inhibitors such as glufosinate; auxin herbicides such as 2,4-D, dicamba; and herbicides such as bromoxynil.

Examples of the plant conferred with a herbicide tolerance by gene recombination technology include glyhosate-tolerant genetically modified plants which have been introduced with one or more gene selected from glyphosate tolerant EPSPS gene (CP4 epsps) from Agrobacterium tumefaciens strain CP4; glyphosate metabolizing enzyme gene (gat4601, gat6421) which is a gene of glyphosate metabolizing enzyme (glyphosate N-acetyl transferase) from Bacillus (Bacillus licheniformis) modified by gene shuffling to enhance the metabolic activity; glyphosate metabolizing enzyme (glyphosate oxidase gene, goxv247) from Ochrobactrum (Ochrobactrum anthropi strain LBAA), or EPSPS gene having glyphosate-tolerant mutation (mepsps, 2mepsps) from corn. There are glyphosate-tolerant genetically modified varieties with respect to plants such as corn (Zea mays L.), soybean (Glycine max L.), cotton (Gossypium hirsutum L.), sugar beet (Beta vulgaris), canola (Brassica napes, Brassica rapa), alfalfa (Medicago sativa), potato (Solanum tuberrosum L), wheat (Triticum aestivum), and creeping bent grass (Agrostis stolonifera).

Some glyphosate-tolerant genetically modified plants are commercially available. For example, a genetically modified plant expressing glyphosate-tolerant EPSPS from Agrobacterium has been marketed under the trade name such as Roundup Ready®, a genetically modified plant expressing glyphosate metabolizing enzyme from Bacillus with enhanced metabolic activity by gene shuffling has been marketed under the trade name such as Optimum® GAT®, Optimum® Gly canola, and a genetically modified plant expressing EPSPS gene having glyphosate-tolerant mutation has been marketed under the trade name GlyTol®.

Examples of plants conferred with herbicide-tolerance by gene recombination technology include glufosinate-tolerant genetically modified plants which have been introduced with phosphinothricin N-acetyltransferase (PAT) gene (bar) of the glufosinate metabolizing enzyme from Streptomyces (Streptomyces hygroscopicus), phosphinothricin N-acetyltransferase gene (pat) of the glufosinate metabolizing enzyme from Streptomyces (Streptomyces viridochromogenes), a synthesized pat gene, or the like. There are glufosinate-tolerant genetically modified varieties with respect to plants such as corn, soybean, cotton, canola, rice (Oryza sativa L.), sugar beet, and cichory (Cichori intybus).

Some glufosinate-tolerant genetically modified plants are commercially available. A genetically modified plant expressing glufosinate metabolizing enzyme (bar, pat) from Streptomyces has been marked under a trade name including LibertyLink®.

Examples of herbicide-tolerant genetically modified plants include genetically modified plants which have been introduced with the gene (bxn) of nitrilase, which is a bromoxynil-metabolizing enzyme from Klebsiella (Klebsiella pneumoniae subsp. Ozaenae). Bromoxynil-tolerant genetically modified varieties have been produced for plants such as canola, cotton, tobacco (Nicotiana tabacum L.) and have been marked under a trade name including Navigator® canola, or BXN®.

Examples of herbicide-tolerant genetically modified plants include genetically modified carnation (Dianthus caryophyllus) which has been introduced with ALS herbicide-tolerant ALS gene (SurB, S4-HrA) from tobacco as a selectable marker. Also, a genetically modified larvae (Linum usitatissumum L.) which has been introduced with ALS herbicide-tolerant ALS gene from Arabidopsis (Arabidopsis thaliana) has been developed under the trade name CDC Triffid Flax. Also, a genetically modified soybean which has been introduced with ALS herbicide-torelant ALS gene (csr1-2) from *Arabidopsis* has been developed under the trade name Cultivance®. Furthermore, there are sulfonylurea/imidazolinone herbicide-tolerant genetically modified corn which has been introduced with ALS herbicide-tolerant ALS gene (zm-hra) from corn, and sulfonylurea herbicide-tolerant genetically modified soybean which has been introduced with ALS herbicide-tolerant ALS gene (gm-hra) from soybean.

Examples of plants conferred with herbicide-tolerance by gene recombination technology include isoxaflutole-tolerant genetically modified soybean which has been introduced with HPPD herbicide-tolerant HPPD gene (hppdPFW 336) from *Pseudomonas* (*Pseudomonas fluorescens* strain A32) and mesotrione-tolerant genetically modified soybean which has been introduced with HPPD gene (avhppd-03) from oats (*Avena sativa*).

Examples of plants conferred with herbicide-tolerance by gene recombination technology include 2,4-D-tolerant genetically modified corns, genetically modified soybeans, genetically modified cottons which have been introduced with gene (aad-1) of 2,4-D metabolizing enzyme aryloxyalkanoate dioxygenase from *Sphingobium* (*Sphingobium herbicidovorans*) or with gene (aad-12) of 2,4-D metabolizing enzyme aryloxyalkanoate dioxygenase from *Delftia* (*Delftia acidovorans*). Some of them are developed under the trade names such as Enlist® Maize, Enlist® Soybean. Also, there are dicamba-tolerant genetically modified soybeans and cottons which have been introduced with gene (dmo) of dicamba monooxygenase, which is dicamba metabolizing enzyme from *Stenotrophomonas* (*Stenotrophomonas maltophilia* strain DI-6).

Examples of genetically modified plant tolerant to two or more herbicides include geneticaly modified cotton and genetically modified corn, which are tolerant to both glyphosate and glufosinate, and marketed under the trade name such as GlyTol® LibertyLink®, Roundup Ready® LibertyLink® Maize. Also, there are a genetically modified soybean tolerant to both glufosinate and 2,4-D and developed under the trade name Enlist® Soybean, and a genetically modified cotton tolerant to both glufosinate and 2,4-D. A genetically modified soybean tolerant to both glyphosate and dicamba has been developed under the trade name Genuity®) Roundup Ready® 2 Xtend®. Genetically modified corn and soybean resistant to both glyphosate and ALS inhibitors have been developed under the trade name Optimum® GAT®. In addition, a genetically modified cotton tolerant to both glufosinate and dicamba, a genetically modified corn tolerant to both glyphosate and 2,4-D, a genetically modified soybean tolerant to both glyphosate and HPPD herbicide have also been developed. Furthermore, a genetically modified soybean tolerant to three herbicides glyphosate, glufosinate and 2,4-D has been developed.

Examples of the plant conferred with a pest resistance by gene recombination technology include plants conferred with resistance to lepidopteran insects, coccinella insects, multipter insects, nematodes and the like.

Examples of the plant conferred with a pest resistance to lepidopteran insects by genetic recombination technology include genetically modified plants such as soybean, cotton, rice, poplar (*Populus* sp.), and tomato (*Lycopersicon esculentum*), and eggplant (*Solanum melongena*), which have been introduced with a gene encoding delta-endotoxin, which is an insecticidal protein derived from a soil bacterium *Bacillus thuringiensis* bacteria (hereinafter referred to as Bt bacteria). Examples of the delta-endotoxin that confers a pest resistance to lepidopteran insects include Cry1A, Cry1Ab, modified Cry1Ab (truncated Cry1Ab), Cry1Ac, Cry1Ab-Ac (hybrid protein of Cry1Ab and Cry1Ac), Cry1C, Cry1F, Cry1Fa2 (modified cry1F), moCry1F (modified Cry1F), Cry1A. 105 (hybrid protein of Cry1Ab, Cry1Ac and Cry1F), Cry2Ab2, Cry2Ae, Cry9C, Vip3A, Vip3Aa20, and the like.

Examples of the plant conferred with a pest resistance to coccinella insects by genetic recombination technology include genetically modified plants such as corn, potato, which have been introduced with a gene encoding delta-endotoxin, which is an insecticidal protein derived from a soil bacterium Bt bacteria. Examples of the delta-endotoxin that confers a pest resistance to coccinella insects include Cry3A, mCry3A (modified Cry3A), Cry3Bb1, Cry34Ab1, and Cry35Ab1.

Examples of the plant conferred with a pest resistance to multipter insects by genetic recombination technology include genetically modified corn, which has been introduced with a synthetic gene encoding a hybrid protein eCry3.1Ab, which is a hybrid protein of Cry3A and Cry1Ab derived from soil bacteria Bt bacteria, a genetically modified cotton, which has been introduced with a gene encoding trypsin inhibitor CpTI from black-eyed pea (*Vigna unguiculata*), a genetically modified poplar, which has been introduced with a gene encoding API, which is a protease inhibitor protein A from arrowhead (*Sagittaria sagittifolia*).

Examples of the insecticidal protein that confers a pest resistance to the plants include hybrid proteins, truncated proteins, and modified proteins of the insecticidal proteins described above. The hybrid proteins are produced by combining different domains of multiple insecticidal proteins using a common recombination technology, and Cry1Ab-Ac and Cry1A.105 are known.

Examples of the truncated proteins include Cry1Ab lacking the amino acid sequence partially. Examples of the modified proteins include proteins in which one or more amino acids of natural delta-endotoxin have been substituted, such as Cry1Fa2, moCry1F, mCry3A.

Examples of other insecticidal proteins that confer insect resistance to plants by genetic recombination technology include insecticidal proteins from *Bacillus cereus* or *Bacillus popilliae*, the insecticidal proteins Vip 1, Vip 2, Vip 3 of Bt bacteria, insecticidal proteins from nematode, toxin produced by an animal such as scorpotoxin, spider toxin, bee venom or insect-specific neurotoxin, toxins of filamentous fungi, plant lectin, agglutinin, protease inhibitor such as trypsin inhibitor, serine protease inhibitor, patatin, cystatin, papain inhibitor, ribosome inactivating protein (RIP) such as ricin, corn-RIP, abrin, rufin, saporin, bryodin, steroid metabolizing enzymes such as 3-hydroxysteroid oxidase, ecdysteroid-UDP-glucosyltransferase, cholesterol oxidase, ecdysone inhibitor, HMG-CoA reductase, ion channel inhibitors such as sodium channel inhibitor, calcium channel inhibitor, juvenile hormone esterase, diuretic hormone receptor, stilbene synthase, bibenzyl synthase, chitinase, glucanase, and the like.

Genetically modified plants conferred with a pest resistance by introducing one or more insecticidal protein gene are known, and some of such genetically modified plants are commercially available.

Examples of commercially available genetically modified cotton conferred with a pest resistance include Bollgard® cotton expressing the insecticidal protein Cry1Ac of Bt bacteria, Bollgard II® cotton expressing the insecticidal proteins Cry1Ac and Cry2Ab of Bt bacteria, Bollgard III® expressing the insecticidal proteins Cry1Ac, Cry2Ab, Vip3A of Bt bacteria, VIPCOT® expressing the insecticidal proteins Vip3A and Cry1Ac of Bt bacteria, WideStrike® expressing the insecticidal proteins Cry1Ac, Cry1F of Bt bacterium.

Examples of commercially available genetically modified corn conferred with a pest resistance include YieldGard® Rootworm RW expressing the insecticidal protein Cry3Bb1 of Bt bacteria, YieldGard Plus® expressing the insecticidal proteins Cry1Ab and Cry3Bb1 of Bt bacteria, YieldGard® VT Pro® expressing the insecticidal proteins Cry1A.105 and Cry2Ab2 of Bt bacteria. Agrisure® RW expressing the insecticidal protein mCry3A of Bt bacteria, Agrisure® Viptera expressing the insecticidal protein Vip3Aa20 of Bt bacteria, Agrisure® Duracade® expressing the insecticidal protein eCry3.1Ab of Bt bacteria are also commercially available.

Examples of commercially available genetically modified potato conferred with a pest resistance include Atlantic NewLeaf® potato, NewLeaf® Russet Burbank potato, and the like, which express the insecticidal protein Cry3A of Bt bacteria.

Examples of genetically modified plants conferred with resistance to plant diseases include kidney bean (*Phaseolus vulgaris*), papaya (*Carica papaya*), plum (*Prunus domestica*), potato, squash (*Cucurbita pepo*), sweet pepper (*Capsicum annuum*), tomato, and the like, which have been conferred with a resistance to plant viral diseases. Specific examples of genetically modified plants conferred with a resistance to plant viral diseases include a genetically modified kidney bean which has been introduced with a gene that produces double-stranded RNA of a replication protein of bean golden mosaic virus, a genetically modified *papaya* which has been introduced with a coat protein gene of *papaya* ringspot virus, a genetically modified potato which has been introduced with a coat protein gene of potato virus Y or replication enzyme domain gene of potato leaf roll virus, a genetically modified squash which has been introduced with a coat protein gene of Cucumber mosaic•virus, with a coat protein gene of Watermelon mosaic virus, or with a coat protein gene of Zucchini yellow mosaic virus, a genetically modified sweet pepper and transgenic tomato which has been introduced with a coat protein gene of Cucumber mosaic•virus, and the like.

A genetically modified potato conferred with a resistance to plant viral diseases is commercially available under a trade name including NewLeaf®.

Examples of the plant conferred with a resistance to plant disease also include plants that have been conferred with an ability to produce a selective anti-pathogenic substance using genetic recombination technology. PR proteins are known as an anti-pathogenic substance (PRPs, EP392225). Such anti-pathogenic substance and genetically modified plants that produce the same are described in EP 392225, WO 199533818, EP 353191 and the like. Examples of the anti-pathogenic substance include ion channel inhibitors such as sodium channel inhibitors, calcium channel inhibitors (KP1, KP4, KP6 toxin produced by viruses are known), anti-pathogenic substances produced by microorganisms such as stilbene synthase, bibenzyl synthase, chitinase, glucanase, peptide antibiotics, antibiotics having heterocycles, protein factors involved in plant disease resistance, which is referred to as plant disease resistance genes and described in WO 2003000906.

Examples of genetically modified plant wherein the quality of product has been modified includes genetically modified plants having a modification in lignin production, a modification in oils or fatty acid components, production of phytic acid degrading enzymes, a modification in flower color, a modification in alpha-amylase activity, a modification in amino acids, a modification in starch or carbohydrate components, inhibition of acrylamide production, reduction of black spots due to mechanical damage, anti-allergy, reduction of nicotine production, or retardation of aging or grain-filling.

There is a genetically modified alfalfa wherein the lignin content has been lowered by RNA interference with a gene that generates double-stranded RNA of S-adenosyl-L-methionine: trans-caffeoyl CoA 3-methyltransferase (ccomt) gene of alfalfa related to lignin production.

A genetically modified canola wherein the triacylglyceride content, including lauric acid, has been increased by introducing a gene involved in fatty acid synthesis, 12:0 ACP thioesterase gene of laurier (*Umbellularia californica*), has been developed under the trade name Laurical® Canola.

A genetically modified canola wherein the degradation of endogenous phytic acid has been enhanced by introducing a gene (phyA) of 3-phytase, which is a degrading enzyme of phytic acid of plants from *Aspergillus niger*, has been developed under the trade name Phytaseed® Canola. Also, a genetically modified corn wherein the degradation of endogenous phytic acid has been enhanced by introducing 3-phytase gene (phyA) of *Aspergillus niger* has been developed.

A genetically modified carnation wherein the flower color has been controlled to blue by introducing a gene of dihydroflavonol-4-reductase, which is an enzyme that produces blue pigment delphinidin and its derivative of *petunia* (*Petunia hybrida*), and a flavonoid-3',5'-hydroxylase gene from *petunia*, pansy (*Viola wittrockiana*), salvia (*Salvia splendens*) or carnation is known. Genetically modified carnations with flower color controlled to blue have been developed under the trade name such as Moonldust®, Moonshadow®, Moonshade®, Moonlite®, Moonaqua®, Moonvista®, Moonique®, Moonpearl®, Moonberry Registered trademark), and Moonvelvet®. Also, genetically modified roses with flower color controlled to blue by introducing a gene of anthocyanin-5-acyltransferase, which is an enzyme that produces blue pigment delphinidin and its derivative, from *Torenia* (*Torenia* sp.), and a flavonoid-3', 5'-hydroxylase gene from pansy have been developed.

A genetically modified corn wherein the production of bioethanol has been increased by introducing a gene (Amy797E) of heat-resistant alpha-amylase relating to starch degradation of *Thermococcales* sp. have been developed under the trade name Enogen®.

A genetically modified corn wherein the production of lysine has been increased by introducing a gene (cordapA) of dihydrodipicolinate synthase relating to the production of amino acid lysine of *Corynebacterium glutamicum* has been developed under the trade name including Mavera®.

A genetically modified melon and a genetically modified tomato wherein the shelf life has been improved by introducing a gene (sam-K) of S-adenosylmethionine hydrolase relating to ethylene production by plant hormones from *Escherichia coli* bacteriophage T3 has been developed. Also, genetically modified tomatoes with improved shelf life by introducing a gene that lacks a part of the ACC synthase gene, which is involved in the ethylene production by plant hormones, from tomato, an ACC deaminase gene from *Pseudomonas* (*Pseudomonas chlororaphis*) that degrades the ethylene precursor ACC, a gene that generates double-stranded RNA of polygalacturonase genes which degrades cell wall pectin, or ACC oxidase genes of tomato related to the production of ethylene have been developed. A genetically modified tomato with improved shelf life by introducing a gene that produces double-stranded RNA of polygalacturonase genes of tomato has been developed under the trade name FLAVR SAVR®.

A genetically modified potato, wherein the possibility of decomposition of starch, formation of black spots due to mechanical damage and production of a carcinogen (acrylamide) from heating are lowered by introducing a gene that generates double-stranded RNA of a transcription factor promoting degradation of starch derived from potato, and a gene that generates double-stranded RNA of polyphenol oxidase gene and a gene that generates double-stranded RNA of genes involved in asparagine production from potato, has been developed under a trade mark including Innate®. Also, a genetically modified potato wherein the amylose content is lowered by introducing an antisense gene of starch synthase from potato has been developed under the trade name Amflora®.

A genetically modified rice having alleviation effect on pollinosis with immune tolerance by introducing a gene (7crp) of altered antigenic protein of cedar pollen has been developed.

A genetically modified soybean wherein the oleic acid content is increased by introducing a partial gene (gm-fad2-1) of ω-6 desaturase, which is a fatty acid desaturase enzyme, of soybean to inhibit the gene expression thereof has been developed under the trade name Plenish® or Treus®. Also, a genetically modified soybean wherein the saturated fatty acid content is lowered by introducing a gene (fatb1-A) that generates a double-stranded RNA of acyl-acyl carrier protein-thioesterase and a gene (fad2-1A) that generates a double-stranded RNA of δ-12 desaturase has been developed under the trade name Vistive Gold®. Also, a genetically modified soybean wherein the ω3 fatty acid content is enhanced by introducing a δ-6 desaturase gene (Pj.D6D) of primrose and a δ-12 desaturase gene (Nc.Fad3) of *Neurospora crassa* has been developed.

A genetically modified tobacco wherein the nicotine content is lowered by introducing an antisense gene of quinolinic acid phosphoribosyltransferase (NtQPT1) of tobacco has been developed.

A genetically modified rice, Golden rice, introduced with a phytoene synthase gene (psy) of trumpet *narcissus* (*Narcissus pseudonarcissus*) and a carotene desaturase gene (crt1) of soil bacteria that synthesizes carotenoids (*Erwinia uredovora*), which allow endosperm-specific expression to produce β-carotene in endosperm tissue, whereby a rice containing vitamin A is enabled to be harvested, has been developed.

Examples of the plants in which the fertile trait has been modified by a genetic recombination technique include genetically modified plants conferred with male sterility and fertility restoration. There are genetically modified corn and chicory conferred with male sterility by introducing anther tapetum cell expressing a ribonuclease gene (barnase) of *Bacillus* (*Bacillus amyloliquefaciens*). There is also a genetically modified corn conferred with male sterility by introducing a DNA adenine methyltransferase gene (dam) of *Escherichia coli*. Furthermore, there is a genetically modified corn wherein the sterility has been controlled by introducing alpha-amylase gene (zm-aa1) of corn that confers male sterility and ms45 protein gene (ms45) of corn that confers fertility restoration.

There is a genetically modified canola conferred with a fertility restoring function by introducing anther tapetum cells expressing a ribonuclease inhibitory protein gene (barstar) of *Bacillus*. In addition, there is a genetically modified canola wherein the sterility has been controlled by introducing a ribonuclease gene (barnase) of *Bacillus* that confers a male sterility and a ribonuclease inhibitory protein gene (barstar) of *Bacillus* that confers a fertility restoration.

Examples of the plants conferred with tolerance to environmental stress by a genetic recombination technique include genetically modified plants conferred with tolerance to dryness. A dry tolerant corn which has been introduced with a cold shock protein gene (cspB) of *Bacillus subtilis* has been developed under the trade name Genuity® DroughtGard®. Also, dry tolerant sugar cane which has been introduced with choline dehydrogenase gene (RmBetA) of alfalfa rhizobium (*Rhizobium meliloti*) or *E. coli* (*Escherichia coli*) has been developed.

Examples of the plants wherein a trait related to growth and yield has been modified by genetic recombination technology include genetically modified plants having enhanced growth ability. For example, a genetically modified soybean which has been introduced with a gene of *Arabidopsis* encoding a transcription factor that controls circadian rhythm (bbx32) has been developed.

The plant according to the present invention can be a plant which has been modified using other techniques than genetic recombination technology. More specifically, it may be a plant which has been conferred with tolerance to environmental stress, disease resistance, tolerance to herbicide, insect resistance, or the like, by classical breeding technique, genetic marker breeding technique, genome editing technique, or the like.

Examples of the plant wherein a tolerance to herbicide has been conferred by classical breeding technique or genetic marker breeding technique include corn, rice, wheat, sunflower (*Helianthus annuus*), canola, and lentil beans (*Lens culinaris*), which are resistant to imidazolinone type ALS inhibiting herbicides, such as imazethapyr, and are marketed under the trade name Clearfield®. Also, there is STS soybean, which is a soybean tolerant to sulfonylurea-based herbicide, as an example of plants which has been conferred with a resistance to sulfonyl-based ALS-inhibiting herbicides such as thifensulfuron methyl by genetic marker breeding technique. Also, there is SR corn, which is resistant to sethoxydim, as an example of plants which has been conferred with a resistance to acetyl CoA carboxylase inhibitor, such as trione oxime type herbicide, aryloxyphenoxypropionic acid type herbicide, by genetic marker breeding technique.

Examples of the plants conferred with pest resistance by classic or genetic marker breeding technique include a soybean having Rag 1 (Resistance Aphid Gene 1) gene, which is an aphid resistant gene. Examples of the plants conferred with resistance to nematodes by the classical breeding technique include a soybean conferred with a resistance to Cysto nematode, and a cotton conferred with a resistance to Root Knot nematode.

Examples of the plants which has been conferred with a resistance to plant disease by classic or genetic marker breeding technique include a corn which has been conferred with a resistant to anthracnose stalk rot, a corn which has been conferred with a resistant to Gray leaf spot, a corn which has been conferred with a resistant to Goss's wilt, a corn which has been conferred with a resistant to *Fusarium* stalk rot, a soybean which has been conferred with a resistant to Asian soybean rust, a pepper which has been conferred with a resistant to *Phytophthora*, a lettuce which has been conferred with a resistant to powdery mildew, a tomato which has been conferred with a resistant to Bacterial wilt, a tomato which has been conferred with a resistant to Gemini virus, and a lettuce which has been conferred with a resistant to downy mildew.

As an example of the plants which have been conferred with a tolerance to dryness by classic or genetic marker breeding technique, a dry tolerant corn has been developed under the trade name such as Agrisure Artesian®, Optimum AQUA Max®.

As an example of the plants conferred with a tolerance to herbicide by genomic editing technique, a canola conferred with a tolerance to sulfonylurea herbicide by rapid breed development technology wherein a mutation to confer tolerance to sulfonylurea herbicide has introduced into ALS gene via chimera oligonucleotides of DNA and RNA.

The above plants include a variety which has been conferred with two or more traits, such as tolerance to environmental stress, disease resistance, tolerance to herbicide, pest resistance, growth and yield traits, quality of product, and sterility, using a genetic recombination technology as described above, such as a classic breeding technique, a genetic marker breeding, or a genome editing technique, as well as a variety which has been conferred with two or more traits from parents by crossing the parents, which are genetically modified plants having same or different characteristic. Examples of such plant include genetically modified plants conferred with both of tolerance to herbicide and pest resistance.

For example, as for a genetically modified plant conferred with tolerance to glyphosate and pest resistance, genetically modified cottons, such as Roundup Ready® Bollgard® cotton, Roundup Ready® Bollgard II® cotton, Roundup Ready® Flex® Bollgard II® cotton, Bollgard® IIIx Roundup Ready® Flex®, and VIPCOT® Roundup Ready Flex® Cotton, have been developed. Also, genetically modified soybeans have been developed under the trade name, such as Agrisure® GT/RW, Roundup Ready® YieldGard® maize, Genuity® VT Double Pro®, Genuity® VT Triple Pro®, YieldGard®, YieldGard® CB+RW, YieldGard® VT® Rootworm® RR 2, YieldGard® RW+RR, YieldGard® VT Triple, or YieldGard® Plus with RR. Furthermore, a genetically modified soybean such as Intacta® Roundup Ready® 2 Pro has been developed.

For example, as for genetically modified plants conferred with tolerance to glufosinate and pest resistance, genetically modified cottons have been developed under the trade name, such as Widestrike® Cotton, Twinlink® Cotton, and Fiber-Max® LibertyLink® Bollgard II®. Also, genetically modified corns have been developed under the trade name, such as Agrisure® CB/LL, Agrisure® CB/LL/RW, Agrisure® Viptera® 2100, Agrisure® Viptera® 3100, Bt Xtra Maize, NaturGard Knockout®, Herculex® RW, Herculex® CB, Herculex® XTRA, Starlink® Maize, and Liberty Link® YieldGard® Maize.

For example, as for genetically modified plants conferred with tolerance to glyphosate and glufosinate and pest resistance, genetically modified cottons have been developed under the trade name, such as Widestrike® Roundup Ready® Cotton, Widestrike® Roundup Ready Flex® Cotton, Widestrike® Cotton, Registered trademark)×Roundup Ready Flex®×VIPCOT® Cotton, and Glytol®×Twinlink®. Also, genetically modified corns have been developed under the trade name, such as Agrisure® GT/CB/LL, Agrisure® 3000GT, Agrisure® 3122, Agrisure® Viptera® 3110, Agrisure® Viptera 3111, Agrisure® Viptera® 3220, Agrisure® Duracade® 5122, Agrisure® Duracade® 5222, Optimum® Intrasect, Optimum® TRIsect, Optimum® Intrasect XTRA, Optimum® Intrasect Xtreme, Genuity® martStax®, Power Core®, Herculex® I RR, Herculex® RW Roundup Ready® 2, and Herculex XTRA® RR.

For example, as for genetically modified plants conferred with tolerance to bromoxynil and pest resistance, a genetically modified cottons has been developed under the trade name, such as BXN® Plus Bollgard® Cotton.

Examples of a variety conferred with two or more traits include genetically modified plants conferred with disease resistance and pest resistance. For example, as for genetically modified plants conferred with resistance to potato virus Y and pest resistance, genetically modified potatoes have been developed under the trade name, such as Hi-Lite NewLeaf® Y Potato, NewLeaf® Y Russet Burbank Potato, and Shepody NewLeaf® Y potato. As for genetically modified plants conferred with resistance to potato leaf roll virus and pest resistance, genetically modified potatoes have been developed under the trade name, such as NewLeaf® Plus Russet Burbank Potato.

Examples of a variety conferred with two or more traits include genetically modified plants conferred with tolerance to herbicide and altered product quality. For example, a genetically modified canola and genetically modified corn, which have been conferred with tolerance to glufosinate and fertile trait have been developed under the trade name, such as InVigor® Canola and InVigor® Maize, respectively.

Examples of a variety conferred with two or more traits include genetically modified plants conferred with a pest resistance and altered product quality. For example, a genetically modified corn conferred with resistance to lepidopterous insects and a trait of enhanced lysine production has been developed under the trade name such as Mavera® YieldGard® Maize.

For other Examples of a variety conferred with two or more traits as mentioned above, genetically modified plants conferred with tolerance to herbicide and a trait altering fertility, genetically modified plants conferred with tolerance to herbicide and tolerance to environmental stress, genetically modified plants conferred with tolerance to herbicide and a trait modifying growth and yield, genetically modified plants conferred with tolerance to herbicide, pest resistance, and a trait modifying product quality, genetically modified plants conferred with tolerance to herbicide, pest resistance, and tolerance to environmental stress, have been developed.

Examples of the plant diseases which can be controlled according to the present invention include the followings. Diseases of rice: blast (*Magnaporthe oryzae*), brown spot (*Cochliobolus miyabeanus*), sheath blight (*Rhizoctonia solani*), "Bakanae" disease (*Gibberella fujikuroi*), seedling blight (*Pythium arrhenomanes, Pythium graminicola, Pythium spinosum, Pythium sp., Rhizopus chinensis, Rhizopus oryzae, Trichoderma viride*);

Diseases of wheat: powdery mildew (*Erysiphe graminis*), Fusarium blight (*Fusarium graminearum, F. avenaceum, F. culmorum, F. asiaticum, Microdochium nivale*), rust (*Puccinia striiformis, P. graminis, P. recondita, P. hordei*), snow mold (*Typhula sp., Micronectriella nivalis*), loose smut (*Ustilago tritici, U. nuda*), stinking smut (*Tilletia caries*), eye spot (*Pseudocercosporella herpotrichoides*), scald (*Rhynchosporium secalis*), speckled leaf blotch (*Septoria tritici*), glume blotch (*Leptosphaeria nodorum*), net blotch (*Pyrenophora teres Drechsler*), yellow spot (*Pyrenophora tritici-repentis*), stripe (*Pyrenophora graminea*), Rhizoctonia damping-off (*Rhizoctonia solani*), snow mold (*Typhula ishikariensis, Typhula incarhata, Sclerotinia borealis, Microdochium nivale*), foot lot disease (*Fusarium graminearum*);

Diseases of corn: smut (*Ustilago maydis*), brown spot (*Cochliobulus heterostrophus*), zonate leaf spot (*Gloeocercospora sorghi*), southern rust (*Puccinia polysora*), grey leaf spot (*Cercospora zaea-maydis*), Rhizoctonia danpimg-off (*Rhizoctonia solani*), gibberella ear rot (*Fusarium moniliforme*), anthracnose (*Colletotrichum graminicola*), seedling blight (*Fusarium* spp, *Rhizoctonia solani*);

Diseases of citrus: gray mold (*Botrytis cinerea*), black leaf spot (*Diaporthe citri*), scab (*Elsinoe fawcetti*), fruit rot (*Penicillium digitatum, P. italicum*); brown rot (*Phytophthora parasitica, Phytophthora citrophthora*);

Diseases of apple: Monilia leaf blight (*Monilinia mali*), Valsa canker (*Valsa ceratosperma*), powdery mildew (*Podosphaera leucotricha*), Alternaria blotch (*Alternaria alternate apple pathotype*), scab (*Venturia inaequalis*), anthracnose (*Colletotrichum gloeosporioies, Colletotrichum acutatum*), Phytophthora rot (*Phytophtora cactorum*); blotch (*Diplocarpon mali*); ring rot (*Botryosphaeria berengeriana*);

Diseases of pear: scab (*Venturia nashicola, V. pirina*), black spot (*Alternaria alternate Japanese pear pathotype*), rust (*Gymnosporangium haraeanum*), Phytophthora fruit rot (*Phytophthora cactorum*);

Diseases of peach: brown rot (*Monilinia fructicola*), scab (*Cladosporium carpophilum*), Phomopsis seed decay (*Phomopsis* sp.);

Diseases of grape: anthracnose (*Elsinoe ampelina*), ripe rot (*Colletorichum gloeosporioides, Colletotrichum acutatum*), powdery mildew (*Uncinula necator*), rust (*Phakopsora ampelopsidis*), black rot (*Guignardia bidwellii*), downy mildew (*Plasmopara viticola*), gray mold (*Botrytis cinerea*);

Diseases of persimmon: anthracnose (*Gloeosporium kaki*), leaf spot (*Cercospora kaki, Mycosphaerella nawae*);

Diseases of cucumber: anthracnose (*Colletotrichum orbiculare*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora blight (*Phytophthora* sp.), damping-off (*Pythium* sp.); Rhizoctonia damping-off (*Rhizoctonia solani*), gray mold (*Botrytis cinerea*);

Diseases of tomato: Early blight (*Alternaria solani*), Leaf mold (*Cladosporium flavum*), late blight (*Phytophthora infestans*), leaf spot (*Stemphylium lycoperici*), gray mold (*Botrytis cinerea*);

Diseases of eggplant: brown spot (*Phomopsis vexans*), powdery mildew (*Erysiphe cichoracearum*), gray mold (*Botrytis cinerea*);

Diseases of brassica vegetables: Alternaria leaf spot (*Alternaria japonica*), leaf spot (*Cercosporella brassicae*), Clubroot (*Plasmodiophora brassicae*), downy mildew (*Peronospora parasitica*), root rot (*Phoma lingam*);

Diseases of rapeseed: Sclerotinia rot (*Sclerotinia sclerotiorum*), Alternaria leaf spot (*Alternaria brassicae*), powdery mildew (*Erysiphe cichoracearum*), black leg (*Leptosphaeria maculans*), Rhizoctonia damping-off (*Rhizoctonia solani*);

Diseases of green onion: rust (*Puccinia allii*), Fusarium wilt (*Fusarium oxysoporum*);

Diseases of onion: gray-mold neck rot (*Botrytis allii*), leaf blight (*Botrytis squamosa*), Fusarium basal rot (*Fusarium oxysoporum, Fusarium solani*);

Diseases of soybean: purple stain (*Cercospora kikuchii*), anthracnose (*Elsinoe glycines*), pod and stem blight (*Diaporthe phaseolorum var. Sojae*), brown spot (*Septoria glycines*), leaf spot (*Cercospora sojina*), rust (*Phakopsora pachyrhizi*), Fusarium blight (*Phytophthora sojae*), damping-off (*Rhizoctonia solani*) (*Pythium* spp.), root necrosis (*Rhizoctonia solani*), Fusarium root necrosis (*Fusarium solani*), anthracnose (*Colletotrichum truncatum*), Fusarium blight (*Fusarium oxysporum, F. avenaceum, F. roseum*), Sclerotinia rot (*Sclerotinia sclerotiorum*), gray mold (*Botrytis cinerea*);

Diseases of adzuki bean: gray mold (*Botrytis cinerea*), Sclerotinia rot (*Sclerotinia sclerotiorum*), rust (*Uromyces phaseoli*), anthracnose (*Coletotrichum phaseolorum*);

Diseases of kidney bean: gray mold (*Botrytis cinerea*), Sclerotinia rot (*Sclerotinia sclerotiorum*), anthracnose (*Colletotrichum lindemthianum*), Fusarium wilt (*Fusarium oxysporum*), rust (*Uromyces phaseoli*), angular leaf spot (*Phaeoisariopsis griseola*), Rhizoctonia root necrosis (*Rhizoctonia solani*), aphanomyces root necrosis (*Aphanomyces euteiches*);

Diseases of peanut: leaf spot (*Cercospora personata*), brown leaf spot (*Cercospora arachidicola*), southern blight (*Sclerotium rolfsii*);

Diseases of pea: gray mold (*Botrytis cinerea*), powdery mildew (*Erysiphe pisi*), root necrosis (*Fusarium solani* f. Sp. *Pisi*);

Diseases of potato: early blight (*Alternaria solani*), late blight (*Phytophthora infestans*), powdery scab (*Spongospora subterranea*), pink rot (*Phytophthora erythroseptica*);

Diseases of strawberry: gray mold (*Botrytis cinerea*), powdery mildew (*Sphaerotheca hamuli*), anthracnose (*Glomerella cingulata*);

Diseases of tea: net blister blight (*Exobasidium reticulatum*), white scab (*Elsinoe leucospila*), gray blight (*Pestalotiopsis* sp.), anthracnose (*Colletotrichum theae-sinensis*);

Diseases of cotton: Fusarium wilt (*Fusarium oxysporum*), Fusarium wilt (*Rhizoctonia solani*);

Diseases of tobacco: brown spot (*Alternaria longipes*), powdery mildew (*Erysiphe cichoracearum*), anthracnose (*Colletotrichum tabacum*), downy mildew (*Peronospora tabacina*), black shank (*Phytophthora nicotianae*);

Diseases of sugar beet: brown leaf spot (*Cercospora beticola*), leaf blight (*Thanatephorus cucumeris*), root necrosis (*Thanatephorus cucumeris*), aphanomyces root rot (*Aphanomyces cochlioides*);

Diseases of rose: scab (*Diplocarpon rosae*), powdery mildew (*Sphaerotheca pannosa*), downy mildew (*Peronospora sparsa*), gray mold (*Botrytis cinerea*);

Diseases of Chrysanthemum: brown leaf spot (*Septoria chrysanthemi-indici*), rust (*Septoria chrysanthemi-indici*), downy mildew (*Bremia lactucae*);

Diseases of radish: alternaria leaf spot (*Alternaria brassicicola*);

Disease of turfgrass: dollar spot (*Sclerotinia homeocarpa*), brown patch and large patch (*Rhizoctonia solani*);

Diseases of banana: Sigatoka disease (*Mycosphaerella fijiensis, Mycosphaerella musicola, Pseudocercospora musae*);

Diseases of sunflower: downy mildew (*Plasmopara halstedii*), alternaria leaf spot (*Alternaria helianthi*), southern blight (*Sclerotium rolfsii*), damping-off (*Rhizoctonia solani*), Sclerotinia rot (*Sclerotinia sclerotiorum*), rust (*Puccinia helianthi*);

Diseases of various plants: diseases caused by *Pythium* spp. (*Pythium aphanidermatum, Pythium debarianum, Pythium graminicola, Pythium irregulare, Pythium ultimum*), gray mold (*Botrytis cinerea*), Sclerotinia rot (*Sclerotinia sclerotiorum*); damping-off (*Rhizoctonia solani*).

The present invention can be applied preferably to bacteria in the genus of *Pythium* spp., *Rhizoctonia* spp., and *Fusarium* spp., particularly, *Pythium* spp. and *Rhizoctonia* spp.

EXAMPLES

The invention is described in more detail with reference to the following Preparation Examples, Formulation Examples, Seed Treatment Examples, and Test Examples, which are not intended to limit the scope of the present invention. The term "part" means "part by weight" unless otherwise specified.

Preparation Example 1

A culture broth of the present bacterial strain, which has been cultured by a known technique, is centrifuged according to an ordinary method to separate into a supernatant and a precipitate. The supernatant is removed, and the precipitate is washed with sterilized water to obtain a bacterial mass. The obtained bacterial mass is suspended in water, dried on spray drier, and the resultant dried product is pulverized to obtain a powder of the present bacterial strain.

Preparation Example 2

A culture broth of the present bacterial strain, which has been cultured by a known technique, is frozen at −80° C., freeze-dried and pulverized to obtain a powder of the present bacterial strain.

Preparation Example 3

In a 500 mL Erlenmeyer flask with baffle, a platinum loop scraping of the present bacterial strain, which have been cultured in TSA (an agar medium containing 15 g/L of casein peptone, 5 g/L of soybean peptone, 5 g/L of sodium chloride, and 15 g/L of agar), are inoculated to a liquid medium containing 200 mL TSB (a liquid medium containing 17 g/L of casein peptone, 3 g/L of soybean peptone, 2.5 g/L of glucose, 5 g/L of sodium chloride and 2.5 g/L of $K_2HPO_4$) and incubated at 30° C. for 12 hours to 24 hours to obtain a liquid culture. In a 500 mL volume Erlenmeyer flask with baffle, 2 mL of the liquid culture is inoculated to 200 mL of a fresh TSB and cultured with shaking for 24 hours to 48 hours to obtain a liquid culture of the present bacterial strain (hereinafter referred to as Liquid Culture a). The Liquid Culture a is centrifuged according to a conventional manner to separate into a supernatant and precipitate. After removing the supernatant, the precipitate is washed with sterile water and centrifuged. The supernatant is removed to obtain bacterial cells of the present bacterial strain.

Preparation Example 4

The bacterial cells of the present bacterial strain obtained in Preparation Example 3 are suspended in water, dried on spray drier, and pulverized the resulting dried product to obtain a powder of the present bacterial strain.

Preparation Example 5

The Liquid Culture a is obtained as described in Preparation 3. The Liquid Culture a is frozen at −80° C., and freeze-dried and pulverized to obtain a powder of the present bacterial strain.

Preparation Example 6

In a Erlenmeyer flask with baffle, a platinum loop scraping of the present bacterial strain, which have been cultured in TSA (an agar medium containing 15 g/L of casein peptone, 5 g/L of soybean peptone, 5 g/L of sodium chloride, and 15 g/L of agar), were inoculated to a liquid medium containing 200 mL TSB (a liquid medium containing 17 g/L of casein peptone, 3 g/L of soybean peptone, 2.5 g/L of glucose, 5 g/L of sodium chloride and 2.5 g/L of $K_2HPO_4$) and incubated at 30° C. for 23 hours to obtain a liquid culture. The liquid culture (2% (v/v)) was inoculated to a fresh TSB in a Erlenmeyer flask with baffle and cultured at 30° C. with shaking for 43 hours to obtain a liquid culture of the present bacterial strain (hereinafter referred to as Liquid Culture b). The liquid culture b was centrifuged at 1900×g for 10 min to separate into a supernatant and a precipitate. After removing the supernatant, the precipitate was washed with sterilized water and centrifuged at 1900×g for 10 min. The supernatant is removed to obtain $3.8 \times 10^{11}$ cfu/g of bacterial cells of the present bacterial strain.

Preparation Example 7

The bacterial cells of the present bacterial strain obtained as described in Preparation Example 6 were frozen at −80° C. and freeze-dried. The dried product obtained thus by freeze-drying was pulverized using scoopula to obtain $2.8 \times 10^{12}$ cfu/g of a powder of the present bacterial strain.

Formulation Example 1

To a mixture containing 3 parts of ethaboxam, 5 parts of white carbon, 8 parts of sodium lignin sulfonate and 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 2

To a mixture containing 1 part of tolclofos-methyl, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 3

To a mixture containing 3 parts of metalaxyl, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 4

To a mixture containing 1 part of fludioxonil, 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1 \times 10^{10}$ cfu per 1 g of the formulation, and diatomaceous earth to 100 parts, followed by mixing and grinding to obtain wettable powder.

Formulation Example 5

To a mixture containing 1 part of the present carboxamide compound (1), 5 parts of white carbon, 8 parts of sodium lignin sulfonate, 2 parts of sodium alkyl naphthalene sulfonate are added the powder of the present bacterial strain obtained as described in Preparation Example 1 or 2, in an amount of $1\times10^{10}$ cfu per 1 g of the formulation, and diatomaceous earth to 100 parts, followed by mixing and grinding to obtain wettable powder.

Formulation Example 6

To a mixture containing 15 parts of ethaboxam and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 7

To a mixture containing 5 parts of tolclofos-methyl and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 8

To a mixture containing 15 parts of metalaxyl and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 9

To a mixture containing 5 parts of fludioxonil and 30 parts of white carbon containing 30% by weight of polyoxyethylene alkyl ether sulfate ammonium salt are added the powder of the present bacterial strain obtained as described in Preparation Example 1 or 2, in an amount of $1\times10^{10}$ cfu per 1 g of the formulation, and water to 100 parts, followed by wet-milling to finely milled to obtain a flowable formulation.

Formulation Example 10

Mixing 32.8 parts of water, 37 parts of the carboxamide compound (1), 4.6 parts of polyoxyethylene tristyryl phenyl ether phosphoric acid ester potassium salt/propylene glycol (40/60) and 0.2 part of an emulsion-type silicone antifoamer, followed by finely milling by wet-milling to obtain Suspension A. To 19 parts of water are added 0.4 part of magnesium aluminum silicate, 4.6 parts of propylene glycol, 0.2 part of xanthan gum, and 0.3 part of a preservative containing 1,2-benzisothiazolin-3-one as an active ingredient, followed by stirring to obtain Thickening Agent Solution A. The Suspension A and the Thickening Agent Solution A are mixed to obtain a formulation. The powder of the present bacterial strain obtained as described in Preparation Example 1 or 2, in an amount of $4\times10^{11}$ cfu per 1 g of the formulation, and water to 100 parts are added and finely milled by wet-milling to obtain a flowable formulation.

Formulation Example 11

To a mixture containing 5 parts of white carbon, 8 parts of sodium lignin sulfonate, and 2 parts of sodium alkyl naphthalene sulfonate are added the bacterial cells or the powder of the present bacterial strain obtained as described in any one of Preparation Examples 3 to 5, in an amount of $1\times10^{10}$ cfu per 1 g of the formulation, and diatomaceous earth to 100 parts to obtain a mixture. The mixture is milled to obtain wettable powder of the present bacterial strain.

Formulation Example 12

To 30 parts of white carbon containing 30% by weight of polyoxyethylene alkyl ether sulfate ammonium salt are added the bacterial cells or powder of the present bacterial strain obtained as described in any one of Preparation Examples 3 to 5, in an amount of $1\times10^{10}$ cfu or $1\times10^{12}$ cfu per 1 g of the formulation, and water to 100 parts to obtain a mixture. The mixture is finely milled by wet-milling to obtain a flowable formulation of the present bacterial strain.

Formulation Example 13

To 30 parts of white carbon containing 30% by weight of polyoxyethylene alkyl ether sulfate ammonium salt were added the powder of the present bacterial strain obtained in Preparation Example 7, in an amount of $1\times10^{10}$ cfu or $1\times10^{12}$ cfu per 1 g of the formulation, and water to 100 parts to obtain a mixture. The mixture was finely milled by wet-milling to obtain a flowable formulation of the present bacterial strain.

Seed Treatment Examples are provided below.

Seed Treatment Example 1

To a mixture containing 5 parts of white carbon, 8 parts of sodium lignin sulfonate and 2 parts of sodium alkyl naphthalene sulfonate are added the powder of the present bacterial strain obtained as described in Preparation Example 1, in an amount of $1\times10^{10}$ cfu per 1 g of the obtained formulation, and diatomaceous earth to 100 parts, followed by mixing and grinding to obtain wettable powder of the present bacterial strain.

Soybean seeds are treated by smearing treatment with tolclofos-methyl flowable formulation (42% flowable formulation, trade name: Rizolex, Valent U.S.A. Corporation) in an amount of 0.1 g of tolclofos-methyl per 1 kg of the soybean seeds. The soybean seeds thus treated with tolclofos-methyl are treated by wet powder coating with the wettable of the present bacterial strain in an amount of $1\times10^{10}$ cfu of the present bacterial strain per 1 kg of said soybean seeds.

Seed Treatment Example 2

Soybean seeds are treated by smearing treatment with metalaxyl flowable formulation (33.92% flowable formulation, trade name: Apron XL, Syngenta Crop Protection LLC) in an amount of 0.3 g of metalaxyl per 1 kg of the soybean seeds. The soybean seeds thus treated with metalaxyl are treated by wet powder coating with wettable powder of the present bacterial strain prepared as described in Seed Treatment Example 1, in an amount of $1\times10^{10}$ cfu/kg of the present bacterial strain per 1 kg of said soybean seeds.

Seed Treatment Example 3

To 30 parts of white carbon containing 30 parts of polyoxyethylene alkyl ether sulfate ammonium salt are added a powder of the present bacterial strain obtained as described in Preparation Example 2, in an amount of $1\times10^{10}$ cfu per 1 g of the formulation, and water to 100 parts, and the mixture is finely milled by wet-milling to obtain a flowable formulation of the present bacterial strain.

Soybean seeds are treated by smearing treatment with a liquid mixture containing the flowable formulation of the present bacterial strain ($1\times10^{10}$ cfu per 1 kg of the soybean seeds) and ethaboxam flowable formulation (38.3% flowable formulation, trade name: Intego Solo, Valent U.S.A. Corporation), in an amount of 0.3 g of ethoboxam per 1 kg of the soybean seeds.

Seed Treatment Example 4

Soybean seeds are treated by smearing treatment with a solution of the carboxamide compound (1) in acetone/Tween 20 (weight ratio=95:5) diluted with water, in an amount of 0.1 g of the carboxamide compound (1) per 1 kg of the soybean seeds.

The soybean seeds thus treated with the carboxamide compound (1) are treated by smearing treatment with a flowable formulation of the present bacterial strain prepared as described in Seed Treatment Example 3, in an amount of $1\times10^{10}$ cfu of the present bacterial strain per 1 kg of said soybean seeds.

Seed Treatment Example 5

Corn seeds are treated by smearing treatment with the flowable formulation of the present bacterial strain and metalaxyl prepared as described in Formulation Example 8, in an amount of $2\times10^{10}$ cfu of the present bacterial strain and 0.3 g of metalaxyl per 1 kg of the corn seeds.

Seed Treatment Example 6

Soybean seeds are treated by smearing treatment with the flowable formulation of the present bacterial strain and fludioxonil prepared as described in Formulation Example 9, in an amount of $2\times10^{10}$ cfu of the present bacterial strain and 0.1 g of fludioxonil per 1 kg of the soybean seeds.

Seed Treatment Example 7

Soybean seeds are treated by smearing treatment with tolclofos-methyl flowable formulation (42% flowable formulation, trade name: Rizolex, Valent U.S.A. Corporation), in an amount of 0.1 g of tolclofos-methyl per 1 kg of the soybean seeds. The soybean seeds thus treated with tolclofos-methyl are treated by wet powder coating with wettable powder of the present bacterial strain obtained as described in Formulation Example 11, in an amount of $1\times10^{10}$ cfu of the present bacterial strain per 1 kg of said soybean seeds.

Seed Treatment Example 8

Soybean seeds are treated by smearing treatment with a liquid mixture containing a flowable formulation of the present bacterial strain obtained as described in Formulation Example 12, in an amount of $1\times10^{10}$ cfu of the present bacterial strain per 1 kg of the soybean seeds, and ethaboxam flowable formulation (38.3% flowable formulation, trade name: Intego Solo, Valent U.S.A. Corporation) in an amount of 0.3 g of ethoboxam for 1 kg of the soybean seeds.

Test Examples are provided below.

Test Example 1

In a rotary seed treatment machine (trade name: HEGE11, manufactured by WINTERSTEIGER), corn seeds (variety: yellow dent corn) are treated by smearing treatment with a liquid mixture containing a flowable formulation of the present bacterial strain as obtained in the Seed Treatment Example 3 (adjusted to $1\times10^{10}$ cfu per 1 kg of the corn seeds) and ethaboxam flowable formulation (38.3% flowable formulation, trade name: Intego Solo, Valent U.S.A. Corporation, adjusted to 0.3 g of ethoboxam per 1 kg of the soybean seeds).

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated corn seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment−disease incidence in treated compartment)/disease incidence in untreated compartment]:     Equation 2

The composition of the invention shows a significantly higher controlling effect.

Test Example 2

In a rotary seed treatment machine (trade name: HEGE11, manufactured by WINTERSTEIGER), soybean seeds (variety:"Hatayutaka") are treated by smearing treatment with a liquid mixture containing a flowable formulation of the present bacterial strain as obtained in the Seed Treatment Example 3 (adjusted to $1\times10^{10}$ cfu per 1 kg of the corn seeds) and metalaxyl flowable formulation (33.92% flowable formulation, trade name: Apron XL, Syngenta Crop Protection LLC, adjusted to 0.3 g of metalaxyl per 1 kg of the soybean seeds).

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 3

Soybean seeds (variety:"Hatayutaka") are treated by wet powder coating treatment with the wettable powder of the present bacterial strain and tolclofos-methyl prepared in Formulation Example 2 (adjusted to $1\times10^{11}$ cfu of the present bacterial strain and 0.1 g of tolclofos-methyl per 1 kg of the soybean seeds), with the wettable powder of the present bacterial strain and fludioxonil prepared in Formulation Example 4 (adjusted to $1\times10^{11}$ cfu of the present bacterial strain and 0.1 g of fludioxonil per 1 kg of the soybean seeds) or with the wettable powder of the present bacterial strain and the carboxamide compound (1) prepared in Formulation Example 5 (adjusted to $1\times10^{11}$ cfu of the present bacterial strain and 0.1 g of the carboxamide compound (1) per 1 kg of the soybean seeds).

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 4

Soybean seeds (variety:"Hatayutaka") are treated by wet powder coating treatment with the wettable powder of the present bacterial strain and ethaboxam prepared in Formulation Example 1 (adjusted to $1\times10^{11}$ cfu of the present bacterial strain and 0.3 g of ethaboxam per 1 kg of the soybean seeds) or with the wettable powder of the present bacterial strain and metalaxyl prepared in Formulation Example 3 (adjusted to $1\times10^{11}$ cfu of the present bacterial strain and 0.3 g of metalaxyl per 1 kg of the soybean seeds).

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 5

In a rotary seed treatment machine (trade name: HEGE11, manufactured by WINTERSTEIGER), soybean seeds are treated by smearing treatment with a flowable formulation of the present bacterial strain and tolclofos-methyl prepared in Formulation Example 7 (adjusted to $2\times10^{10}$ cfu of the present bacterial strain and 0.1 g of tolclofos-methyl per 1 kg of the soybean seeds), with a flowable formulation of the present bacterial strain and fludioxonil prepared in Formulation Example 9 (adjusted to $2\times10^{10}$ cfu of the present bacterial strain and 0.3 g of fludioxonil per 1 kg of the soybean seeds), or with a flowable formulation of the present bacterial strain and the carboxamide compound (1) prepared in Formulation Example 10 (adjusted to $2\times10^{10}$ cfu of the present bacterial strain and 0.1 g of the carboxamide compound (1) per 1 kg of the soybean seeds).

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 6

In a rotary seed treatment machine (trade name: HEGE11, manufactured by WINTERSTEIGER), soybean seeds are treated by smearing treatment with the flowable formulation of the present bacterial strain and ethaboxam prepared in Formulation Example 6 (adjusted to $2 \times 10^{10}$ cfu of the present bacterial strain and 0.3 g of ethaboxam per 1 kg of the soybean seeds) or with the flowable formulation of the present bacterial strain and metalaxyl prepared in Formulation Example 8 (adjusted to $2 \times 10^{10}$ cfu of the present bacterial strain and 0.3 g of metalaxyl per 1 kg of the soybean seeds).

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 7

In a rotary seed treatment machine (trade name: HEGE11, manufactured by WINTERSTEIGER), soybean seeds are treated by smearing treatment respectively with a chemical liquid, which has been prepared by dissolving a tolclofos-methyl flowable formulation (42% flowable formulation, trade name: Rizolex, Valent U.S.A. Corporation) in an amount of 0.1 g of tolclofos-methyl per 1 kg of the soybean seeds or a fludioxonil flowable formulation (10% flowable formulation, trade name: Maxim100, Syngenta Crop Protection LLC) in an amount of 0.1 g of fludioxonil per 1 kg of the soybean seeds, or the carboxamide compound (1) in an amount of 0.1 g of fludioxonil per 1 kg of the soybean seeds, in acetone/Tween 20 (weight ratio=95:5), followed by diluting with water. In a rotary seed treatment machine (trade name: HEGE11, manufactured by WINTERSTEIGER), the soybean seeds thus treated with ethaboxam, tolclofos-methyl, fludioxonil or the carboxamide compound (1), respectively, are treated by wet powder coating with the wettable powder of the present bacterial strain obtained in Seed Treatment Example 1 in an amount of $1 \times 10^{10}$ cfu of the present bacterial strain per 1 kg of said soybean seeds.

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The composition of the invention shows a significantly higher controlling effect.

Test Example 8

In a rotary seed treatment machine (trade name: HEGE11, manufactured by WINTERSTEIGER), soybean seeds are treated by smearing treatment with a solution prepared by dissolving a metalaxyl flowable formulation (33.92% flowable formulation, trade name: Apron XL, Syngenta Crop Protection LLC, adjusted to 0.3 g of metalaxyl per 1 kg of the soybean seeds). In a rotary seed treatment machine (trade name: HEGE11, manufactured by WINTERSTEIGER), the soybean seeds thus treated with metalaxyl are treated by wet powder coating with the wettable powder of the present bacterial strain obtained in Seed Treatment Example 1 in an amount of $1 \times 10^{10}$ cfu of the present bacterial strain per 1 kg of said soybean seeds.

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 9

In a rotary seed treatment machine (trade name: HEGE11, manufactured by WINTERSTEIGER), soybean seeds are treated by smearing treatment with the flowable formulation of the present bacterial strain obtained in Seed Treatment Example 3 (adjusted to $1\times10^{10}$ cfu of the present bacterial strain per 1 kg of the soybean seeds). In a rotary seed treatment machine (trade name: HEGE11, manufactured by WINTERSTEIGER), soybean seeds thus treated by smearing treatment are treated with a chemical liquid, which has been prepared by dissolving a tolclofos-methyl flowable formulation (42% flowable formulation, trade name: Rizolex, Valent U.S.A. Corporation, adjusted to 0.1 g of tolclofos-methyl per 1 kg of the soybean seeds) or a fludioxonil flowable formulation (10% flowable formulation, trade name: Maxim100, Syngenta Crop Protection LLC, adjusted to 0.1 g of fludioxonil per 1 kg of the soybean seeds) or the carboxamide compound (1) (adjusted to 0.1 g of fludioxonil per 1 kg of the soybean seeds) in acetone/Tween 20 (weight ratio=95:5), followed by diluting with water, respectively.

A plastic pot is filled with a soil, and then, the treated seeds are seeded and covered with a soil, which has been mixed with damping-off fungus (*Rhizoctonia solani*) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 10

In a rotary seed treatment machine (trade name: HEGE11, manufactured by WINTERSTEIGER), soybean seeds are treated by smearing treatment with a flowable formulation of the present bacterial strain obtained in Seed Treatment Example 3 (adjusted to $1\times10^{10}$ cfu of the present bacterial strain per 1 kg of the soybean seeds). In a rotary seed treatment machine (trade name: HEGE11, manufactured by WINTERSTEIGER), soybean seeds thus treated by smearing treatment are treated with a chemical liquid, which has been prepared by dissolving an ethaboxam flowable formulation (38.3% flowable formulation, trade name: Intego Solo, Valent U.S.A. Corporation, adjusted to 0.3 g of ethaboxam per 1 kg of the soybean seeds) or a metalaxyl flowable formulation (33.92% flowable formulation, trade name: Apron XL, using the Syngenta Crop Protection LLC, adjusted to 0.3 g of metalaxyl per 1 kg of the soybean seeds), respectively.

A plastic pot is filled with a soil, and then, the treated seeds are seeded and covered with a soil, which has been mixed with damping-off fungus (*Pythium* spp.) cultured in a bran medium. Cultivation is carried out in a greenhouse under irrigation ("treated compartment"). The plants are investigated 20 days after for the number of diseased plants, and the disease incidence is calculated by the following "Equation 1". Separately, untreated soybean seeds are seeded, covered with a soil and cultivated in a similar manner as described above for "treated compartment" ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The composition of the invention shows a significantly higher controlling effect.

Test Example 11

A chemical liquid is prepared by diluting ethaboxam flowable formulation (12.5% flowable formulation, trade name: Ethofin flowable, Nippon Soda Co., Ltd.) with water to 400 ppm of ethaboxam or dissolving metalaxyl in acetone/Tween 20 (weight ratio=95:5) and diluting with water to 400 ppm of metalaxyl, and followed by combining the solution with the equal volume of a solution of the flowable formulation obtained in Seed Treatment Example 1 (adjusted to $2\times10^8$ cfu of the present bacterial strain).

The chemical liquid is sprayed to tomato plants (variety: Campari, 4-leaf stage) in a sufficient amount. After air drying, the plants are inoculated with late blight fungus (*Phytophthora infestans*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)]  Equation:

The composition of the invention shows a significantly higher controlling effect.

Test Example 12

A chemical liquid is prepared by diluting fludioxonil flowable formulation (20% flowable formulation, trade name: Savior flowable, Syngenta Japan) with water to 400 ppm of fludioxonil or dissolving the carboxamide compound (1) in acetone/Tween 20 (weight ratio=95:5) and diluting with water to 400 ppm of the carboxamide compound (1), and followed by combining the solution with the equal volume of a solution of the flowable formulation obtained in Seed Treatment Example 1 (adjusted to $2\times10^8$ cfu of the present bacterial strain).

The chemical liquid is sprayed to cucumber plants (variety: "Sagami Hanjiro", 3-leaf stage) in a sufficient amount. After air drying, the plants are inoculated with gray mold fungus (*Botrytis cinerea*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)] Equation:

The composition of the invention shows a significantly higher controlling effect.

Test Example 13

A chemical liquid is prepared by diluting tolclofos-methyl wettable powder (50% wettable powder, trade name: Rizolex 50, Sumitomo Chemical Co., Ltd.) with water to 400 ppm of tolclofos-methyl or dissolving the carboxamide compound (1) in acetone/Tween 20 (weight ratio=95:5) and diluting with water to 400 ppm of the carboxamide compound (1), and followed by combining the solution with the equal volume of a solution of the flowable formulation obtained in Seed Treatment Example 1 (adjusted to $2\times10^8$ cfu of the present bacterial strain).

The chemical liquid is sprayed to sugar beet plants (variety: "Yukimaru", growth stage) in a sufficient amount. After air drying, the plants are inoculated with leaf blight fungus (*Thanatephorus cucumeris*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)] Equation:

The composition of the invention shows a significantly higher controlling effect.

Test Example 14

A chemical liquid is prepared by dissolving the carboxamide compound (1) in acetone/Tween 20 (weight ratio=95:5) and diluting with water to 400 ppm of the carboxamide compound (1), and followed by combining the solution with the equal volume of a solution of the flowable formulation obtained in Seed Treatment Example 1 (adjusted to $2\times10^8$ cfu of the present bacterial strain).

The chemical liquid is sprayed to wheat plants (cultivar: Apogee, growth stage) in a sufficient amount. After air drying, the plants are inoculated with leaf blight fungus (*Septoria tritici*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)] Equation:

The composition of the invention shows a significantly higher controlling effect.

Test Example 15

In a rotary seed treatment machine (trade name: HEGE11, manufactured by WINTERSTEIGER), corn seeds (variety: yellow dent corn) are treated by smearing treatment using a flowable formulation of the present bacterial strain as obtained in Formulation Example 12 and ethaboxam flowable formulation (38.3% flowable formulation, trade name: Intego Solo, Valent U.S.A. Corporation), so that the soybean seeds retain the present bacterial strain and/or the compound in the amount shown in Table 1.

A plastic pot is filled with a soil, and then, the coon seeds, which have been treated with the present bacterial strain, compound or the present bacterial strain+compound as shown in Table 1, are seeded and covered with a soil, which has been mixed with damping-off fungus (*Pythium* spp.) cultured in a bran medium or grass medium ("treated compartment"). Cultivation is carried out in a greenhouse under irrigation. The plants are investigated 20 days after for the number of diseased plants, and the disease incidence is calculated by the following "Equation 1". Similar procedures are conducted using untreated corn seeds, instead of the treated corn seeds, as described above for the treated compartment ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The compartment treated with the composition of the invention shows a synergistic controlling effect, for each combination of the present bacterial strain and the compound, compared with that of the corresponding compartment treated solely with the present bacterial strain or the compound.

TABLE 1

| Bacteria/Compound retained by Seeds | Retaining Amount (per Kg of seeds) |
|---|---|
| The Present Bacterial strain | $1 \times 10^{10}$ cfu |
| The Present Bacterial strain | $1 \times 10^{12}$ cfu |
| The Present Bacterial strain | $1 \times 10^{7}$ cfu |
| Ethaboxam | 0.00625 g |
| Ethaboxam | 0.025 g |
| Ethaboxam | 0.1 g |
| The Present Bacterial strain | $1 \times 10^{10}$ cfu |
| Ethaboxam | 0.00625 g |
| The Present Bacterial strain | $1 \times 10^{10}$ cfu |
| Ethaboxam | 0.025 g |
| The Present Bacterial strain | $1 \times 10^{10}$ cfu |
| Ethaboxam | 0.1 g |
| The Present Bacterial strain | $1 \times 10^{12}$ cfu |
| Ethaboxam | 0.00625 g |
| The Present Bacterial strain | $1 \times 10^{12}$ cfu |
| Ethaboxam | 0.025 g |
| The Present Bacterial strain | $1 \times 10^{7}$ cfu |
| Ethaboxam | 0.1 g |

Test Example 16

Soybean seeds (variety:"Hatayutaka") are treated by smearing treatment using wettable powder of the present bacterial strain as obtained in Formulation 11, a flowable formulation of the present bacterial strain as obtained in Formulation Example 12, ethaboxam flowable formulation (38.3% flowable formulation, trade name: Intego Solo, Valent U.S.A. Corporation) and metalaxyl flowable formulation (33.92% flowable formulation, trade name: Apron XL, Syngenta Crop Protection LLC), so that the soybean seeds retain the present bacterial strain and/or the compound in the amount shown in Table 2.

A plastic pot is filled with a soil, and then, the coon seeds, which have been treated with the present bacterial strain, compound or the present bacterial strain+compound as shown in Table 2, are seeded and covered with a soil, which has been mixed with damping-off fungus (*Pythium* spp.) cultured in a bran medium or grass medium ("treated compartment"). Cultivation is carried out in a greenhouse under irrigation. The plants are investigated 20 days after for the number of diseased plants, and the disease incidence is calculated by the following "Equation 1". Similar procedures are conducted using untreated corn seeds, instead of the treated corn seeds, as described above for the treated compartment ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds):     Equation 1

Control value (%)=100×[(disease incidence in untreated compartment disease incidence in treated compartment)/disease incidence in untreated compartment]:     Equation 2

The compartment treated with the composition of the invention shows a synergistic controlling effect, for each combination of the present bacterial strain and the compound, compared with that of the corresponding compartment treated solely with the present bacterial strain or the compound.

TABLE 2

| Bacteria/Compound retained by Seeds | Retaining Amount (/Kg seeds) |
|---|---|
| The Present Bacterial strain | $1 \times 10^{10}$ cfu |
| The Present Bacterial strain | $1 \times 10^{8}$ cfu |
| The Present Bacterial strain | $1 \times 10^{6}$ cfu |
| Ethaboxam | 0.075 g |
| Ethaboxam | 0.15 g |
| Ethaboxam | 0.3 g |
| Metalaxyl | 0.01 g |
| Metalaxyl | 0.04 g |
| Metalaxyl | 0.16 g |
| The Present Bacterial strain | $1 \times 10^{10}$ cfu |
| Ethaboxam | 0.075 g |
| The Present Bacterial strain | $1 \times 10^{10}$ cfu |
| Ethaboxam | 0.15 g |
| The Present Bacterial strain | $1 \times 10^{10}$ cfu |
| Ethaboxam | 0.3 g |
| The Present Bacterial strain | $1 \times 10^{10}$ cfu |
| Metalaxyl | 0.01 g |
| The Present Bacterial strain | $1 \times 10^{10}$ cfu |
| Metalaxyl | 0.04 g |
| The Present Bacterial strain | $1 \times 10^{10}$ cfu |
| Metalaxyl | 0.16 g |
| The Present Bacterial strain | $1 \times 10^{8}$ cfu |
| Ethaboxam | 0.3 g |
| The Present Bacterial strain | $1 \times 10^{6}$ cfu |
| Metalaxyl | 0.01 g |
| The Present Bacterial strain | $1 \times 10^{8}$ cfu |
| Metalaxyl | 0.16 g |

Test Example 17

In a rotary seed treatment machine (trade name: HEGE11, manufactured by WINTERSTEIGER), soybean seeds (variety: "Hatayutaka") are treated by smearing treatment using a chemical liquid, which has been prepared by dissolving a tolclofos-methyl flowable formulation (42% flowable formulation, trade name: Rizolex, Valent U.S.A. Corporation), a fludioxonil flowable formulation (10% flowable formulation, trade name: Maxim100, Syngenta Crop Protection LLC) or the carboxamide compound (1) dissolved in acetone/Tween 20 (weight ratio=95:5) and diluted with water, as well as wettable powder of the present bacterial strain as obtained in Formulation Example 11 and a flowable formulation of the present bacterial strain as obtained in Formulation Example 12, so that the soybean seeds retain the present bacterial strain and/or the compound in the amount shown in Table 3.

In a rotary seed treatment machine (trade name: HEGE11, manufactured by WINTERSTEIGER), soybean seeds thus treated with tolclofos-methyl, fludioxonil or the carboxamide compound (1) are treated with wettable powder of the present bacterial strain as obtained in Formulation Example 11 or a flowable formulation of the present bacterial strain as obtained in Formulation Example 12, so that the soybean seeds retain the amount shown in Table 3.

A plastic pot is filled with a soil, and then, the coon seeds, which have been treated with the present bacterial strain, compound or the present bacterial strain+compound as shown in Table 3, are seeded and covered with a soil, which has been mixed with damping-off fungus (*Rhizoctonia solani*) cultured in a bran medium ("treated compartment"). Cultivation is carried out in a greenhouse under irrigation. The plants are investigated 20 days after for the number of diseased plants, and the disease incidence is calculated by the following "Equation 1". Similar procedures are conducted using untreated corn seeds, instead of the treated corn seeds, as described above for the treated compartment ("untreated compartment"). The plants are investigated 20 days after for the number of diseased plants, and the disease incidence is calculated by the following "Equation 1". Based on the disease incidences of the treated compartment and the untreated compartment, the control value of the treated compartment is calculated by the following equation "Equation 2", and the treated compartment is confirmed to have a good control effect on plant disease.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

The compartment treated with the composition of the invention shows a synergistic controlling effect, for each combination of the present bacterial strain and the compound, compared with that of the corresponding compartment treated solely with the present bacterial strain or the compound.

TABLE 3

| Bacteria/Compound retained by Seeds | Retaining Amount (/Kg seeds) |
|---|---|
| The Present Bacterial strain | 1 × $10^{10}$ cfu |
| The Present Bacterial strain | 1 × $10^{6}$ cfu |
| The Present Bacterial strain | 1 × $10^{7}$ cfu |
| The Present Bacterial strain | 1 × $10^{11}$ cfu |
| Tolclofos-Methyl | 0.01 g |
| Tolclofos-Methyl | 0.05 g |
| Tolclofos-Methyl | 0.25 g |
| Fludioxonil | 0.004 g |
| Fludioxonil | 0.02 g |
| Fludioxonil | 0.1 g |
| The Carboxamide Compound (1) | 0.0004 g |
| The Carboxamide Compound (1) | 0.002 g |
| The Carboxamide Compound (1) | 0.01 g |
| The Present Bacterial strain | 1 × $10^{10}$ cfu |
| Tolclofos-Methyl | 0.01 g |
| The Present Bacterial strain | 1 × $10^{10}$ cfu |
| Tolclofos-Methyl | 0.05 g |
| The Present Bacterial strain | 1 × $10^{10}$ cfu |
| Tolclofos-Methyl | 0.25 g |
| The Present Bacterial strain | 1 × $10^{10}$ cfu |
| Fludioxonil | 0.004 g |
| The Present Bacterial strain | 1 × $10^{10}$ cfu |
| Fludioxonil | 0.02 g |
| The Present Bacterial strain | 1 × $10^{10}$ cfu |
| Fludioxonil | 0.1 g |
| The Present Bacterial strain | 1 × $10^{10}$ cfu |
| The Carboxamide Compound (1) | 0.0004 g |
| The Present Bacteria | 1 × $10^{10}$ cfu |
| The Carboxamide Compound (1) | 0.002 g |
| The Present Bacteria | 1 × $10^{10}$ cfu |
| The Carboxamide Compound (1) | 0.01 g |
| The Present Bacterial strain | 1 × $10^{6}$ cfu |
| Tolclofos-Methyl | 0.01 g |
| The Present Bacterial strain | 1 × $10^{7}$ cfu |
| Tolclofos-Methyl | 0.05 g |
| The Present Bacterial strain | 1 × $10^{6}$ cfu |
| Fludioxonil | 0.004 g |
| The Present Bacterial strain | 1 × $10^{7}$ cfu |
| Fludioxonil | 0.02 g |
| The Present Bacterial strain | 1 × $10^{7}$ cfu |
| Fludioxonil | 0.1 g |

TABLE 3-continued

| Bacteria/Compound retained by Seeds | Retaining Amount (/Kg seeds) |
|---|---|
| The Present Bacterial strain | 1 × $10^{11}$ cfu |
| The Carboxamide Compound (1) | 0.0004 g |
| The Present Bacterial strain | 1 × $10^{6}$ cfu |
| The Carboxamide Compound (1) | 0.01 g |

Test Example 18

Wettable powder of the present bacterial strain as obtained in Formulation Example 11 or a flowable formulation of the present bacterial strain as obtained in Formulation Example 12, ethaboxam flowable formulation (12.5% flowable formulation, trade name: Ethofin flowable, Nippon Soda Co., Ltd.) and metalaxyl are dissolved in acetone/Tween 20 (weight ratio=95:5) and diluted with water to prepare a chemical solution, and the concentration is adjusted as shown in Table 4 to prepare a spray liquid.

The liquid (50 mL) is sprayed to tomato plants (variety: Campari, 4-leaf stage). After air drying, the plants are inoculated with late blight fungus (*Phytophthora infestans*) and left to stand under moisture condition for 10 days ("treated compartment"). Also, similar procedures are conducted without spraying the liquid ("untreated compartment").

The effect on the treated compartment is determined by the following equation, based on the onset area rates of the treated compartment and the untreated compartment.

controlling effect=100×[1−(onset area rate of treated compartment)/(onset area rate of untreated compartment)] Equation:

The compartment treated with the composition of the invention shows a synergistic controlling effect, for each combination of the present bacterial strain and the compound, compared with that of the corresponding compartment treated solely with the present bacterial strain or the compound.

TABLE 4

| Bacteria/Compound sprayed to Plants | Amount of Bacteria/Compound in Spray Liquid (/L) |
|---|---|
| The Present Bacterial strain | 1 × $10^{8}$ cfu |
| Ethaboxam | 0.4 mg |
| Ethaboxam | 0.8 mg |
| Metalaxyl | 1.5 mg |
| Metalaxyl | 3 mg |
| The Present Bacterial strain | 1 × $10^{8}$ cfu |
| Ethaboxam | 0.4 mg |
| The Present Bacterial strain | 1 × $10^{8}$ cfu |
| Ethaboxam | 0.8 mg |
| The Present Bacterial strain | 1 × $10^{8}$ cfu |
| Metalaxyl | 1.5 mg |
| The Present Bacterial strain | 1 × $10^{8}$ cfu |
| Metalaxyl | 3 mg |

Test Example 19

Wettable powder of the present bacterial strain as obtained in Formulation Example 11 or a flowable formulation of the present bacterial strain as obtained in Formulation Example 12, fludioxonil flowable formulation (20% flowable formulation, trade name: Savior flowable, Syngenta Japan) and the carboxamide compound (1) are dissolved in acetone/Tween 20 (weight ratio=95:5) and diluted with water to prepare a chemical solution, and the concentration is adjusted as shown in Table 5 to prepare a spray liquid.

The liquid (50 mL) is sprayed to cucumber plants (variety: "Sagami Hanjiro", 2-leaf stage). After air drying, the plants are inoculated with gray mold fungus (*Botrytis cinerea*) and left to stand under moisture condition for 10 days ("treated compartment"). Also, similar procedures are conducted without spraying the liquid ("untreated compartment").

The effect on the treated compartment is determined by the following equation, based on the onset area rates of the treated compartment and the untreated compartment.

controlling effect=100×[1−(onset area rate of treated compartment)/(onset area rate of untreated compartment)]   Equation:

The compartment treated with the composition of the invention shows a synergistic controlling effect, for each combination of the present bacterial strain and the compound, compared with that of the corresponding compartment treated solely with the present bacterial strain or the compound.

TABLE 5

| Bacteria/Compound sprayed to Plants | Amount of Bacteria/Compound in Spray Liquid (/L) |
|---|---|
| The Present Bacterial strain | 1 × 10$^8$ cfu |
| Fludioxonil | 0.5 mg |
| Fludioxonil | 1 mg |
| The Carboxamide Compound (1) | 1 mg |
| The Carboxamide Compound (1) | 4 mg |
| The Present Bacterial strain | 1 × 10$^8$ cfu |
| Fludioxonil | 0.5 mg |
| The Present Bacterial strain | 1 × 10$^8$ cfu |
| Fludioxonil | 1 mg |
| The Present Bacterial strain | 1 × 10$^8$ cfu |
| The Carboxamide Compound (1) | 1 mg |
| The Present Bacterial strain | 1 × 10$^8$ cfu |
| The Carboxamide Compound (1) | 4 mg |

Test Example 20

A chemical liquid prepared by diluting tolclofos-methyl wettable powder (50% wettable powder, trade name: Rizolex 50, Sumitomo Chemical Co., Ltd.) with water to 0.5 ppm or 2.5 ppm of tolclofos-methyl is combined with the equal volume of a solution of wettable powder of the present bacterial strain as obtained in Formulation 11 or of a flowable formulation of the present bacterial strain as obtained in Formulation Example 12 (adjusted to 1×10$^8$ cfu of the present bacterial strain per 1 L of the liquid to be sprayed) ("treated compartment"). Also, similar procedures are conducted without spraying the liquid ("untreated compartment").

The liquid (50 mL) is sprayed to sugar beet plants (variety: "Yukimaru", growth stage). After air drying, the plants are inoculated with leaf blight fungus (*Thanatephorus cucumeris*) and left to stand under moisture condition for 10 days.

The effect on the treated compartment is determined by the following equation, based on the onset area rates of the treated compartment and the untreated compartment.

controlling effect=100×[1−(onset area rate of treated compartment)/(onset area rate of untreated compartment)]   Equation:

The compartment treated with the composition of the invention shows a synergistic controlling effect, for each combination of the present bacterial strain and the compound, compared with that of the corresponding compartment treated solely with the present bacterial strain or the compound.

Test Example 21

In a rotary seed treatment machine (trade name: HEGE11, manufactured by WINTERSTEIGER), corn seeds (variety: yellow dent corn) were treated by smearing treatment using a flowable formulation of the present bacterial strain as obtained in Formulation Example 13 and ethaboxam flowable formulation (34.6% flowable formulation, Valent U.S.A. Corporation), so that the soybean seeds retain the present bacterial strain and/or the compound in the amount shown in Table 6.

A plastic pot was filled with a soil, and then, the coon seeds, which have been treated with the present bacterial strain, compound or the present bacterial strain+compound as shown in Table 6, were seeded and covered with a soil, which has been mixed with damping-off fungus (*Pythium* spp.) cultured in a bran medium or grass medium ("treated compartment"). Cultivation was carried out in a greenhouse under irrigation. Also, similar procedures were conducted using untreated corn seeds, instead of the treated corn seeds, as described above for the treated compartment ("untreated compartment"). The plants were investigated 20 days after for the number of diseased plants, and the disease incidence was calculated by the following "Equation 1". The control value of the treated compartment was calculated by the following equation "Equation 2", based on the disease incidences of the treated compartment and the untreated compartment.

Disease incidence (%)=100×(number of diseased plant/total number of seeded seeds):   Equation 1

Control value (%)=100×[(disease incidence in untreated compartment disease incidence in treated compartment)/disease incidence in untreated compartment]:   Equation 2

TABLE 6

| Bacteria/Compound retained by Seeds | Retaining Amount (/kg seeds) | Control Value | Estimated Value* |
|---|---|---|---|
| The Present Bacterial strain | 1 × 10$^{10}$ cfu | 9.7 | — |
| The Present Bacterial strain | 1 × 10$^{12}$ cfu | 12.9 | — |
| The Present Bacterial strain | 1 × 10$^{7}$ cfu | 3.2 | — |
| Ethaboxam | 0.00625 g | 19.4 | — |
| Ethaboxam | 0.025 g | 32.3 | — |
| Ethaboxam | 0.1 g | 48.4 | — |
| The Present Bacterial strain<br>Ethaboxam | 1 × 10$^{10}$ cfu<br>0.00625 g | 35.5 | 27.2 |
| The Present Bacterial strain<br>Ethaboxam | 1 × 10$^{10}$ cfu<br>0.025 g | 48.4 | 38.8 |
| The Present Bacterial strain<br>Ethaboxam | 1 × 10$^{10}$ cfu<br>0.1 g | 77.4 | 53.4 |
| The Present Bacterial strain<br>Ethaboxam | 1 × 10$^{12}$ cfu<br>0.00625 g | 51.6 | 29.8 |
| The Present Bacterial strain<br>Ethaboxam | 1 × 10$^{12}$ cfu<br>0.025 g | 67.7 | 40.1 |
| The Present Bacterial strain<br>Ethaboxam | 1 × 10$^{7}$ cfu<br>0.1 g | 71.0 | 50.0 |

*Control value estimated from the calculation by the Colby's equation

If the effect by the combination of two active ingredients is greater than that of the estimated value E, which is calculated by the Colby's equation as follows, the effect is regarded as synergistic.

$$E = X + Y - X \cdot Y/100$$

wherein,

E=Control value when using the mixture of the active ingredients A and B at the concentrations m and n (amount of the active ingredient), respectively.

X=Control value when using the active ingredient A at the concentration m (amount of the active ingredient).

Y=Control value when using the active ingredient B at the concentration n (amount of the active ingredient).

The compartment treated with the composition of the invention showed a synergistic controlling effect, for each combination of the present bacterial strain and the compound, compared with that of the corresponding compartment treated solely with the present bacterial strain or the compound.

Test Example 22

Soybean seeds (variety:"Hatayutaka") were treated by smearing treatment using a flowable formulation of the present bacterial strain as obtained in Formulation Example 13, ethaboxam flowable formulation (34.6% flowable formulation, Valent U.S.A. Corporation) and metalaxyl flowable formulation (30.14% flowable formulation, trade name: Sebring, Nufarm), so that the soybean seeds retain the present bacterial strain and/or the compound in the amount shown in Table 7.

A plastic pot was filled with a soil, and then, the soybean seeds, which have been treated with the present bacterial strain, compound or the present bacterial strain+compound as shown in Table 7, were seeded and covered with a soil, which has been mixed with damping-off fungus (*Pythium* spp.) cultured in a bran medium or grass medium ("treated compartment"). Cultivation was carried out in a greenhouse under irrigation. Also, similar procedures were conducted using untreated soybean seeds, instead of the treated soybean seeds, as described above for the treated compartment ("untreated compartment"). The plants were investigated 20 days after for the number of diseased plants, and the disease incidence was calculated by the following "Equation 1". The control value of the treated compartment was calculated by the following equation "Equation 2", based on the disease incidences of the treated compartment and the untreated compartment.

Disease incidence (%)=100×(number of diseased plant/total number of seeded seeds): Equation 1

Control value (%)=100×[(disease incidence in untreated compartment disease incidence in treated compartment)/disease incidence in untreated compartment]: Equation 2

TABLE 7

| Bacteria/Compound retained by Seeds | Retaining Amount (/kg seeds) | Control Value | Estimated Value* |
|---|---|---|---|
| The Present Bacterial strain | $1 \times 10^{10}$ cfu | 12.5 | — |
| The Present Bacterial strain | $1 \times 10^{8}$ cfu | 9.4 | — |
| The Present Bacterial strain | $1 \times 10^{6}$ cfu | 3.1 | — |
| Ethaboxam | 0.075 g | 46.9 | — |
| Ethaboxam | 0.15 g | 56.2 | — |
| Ethaboxam | 0.3 g | 62.5 | — |
| Metalaxyl | 0.01 g | 40.6 | — |
| Metalaxyl | 0.04 g | 50.0 | — |
| Metalaxyl | 0.16 g | 59.4 | — |
| The Present Bacterial strain Ethaboxam | $1 \times 10^{10}$ cfu 0.075 g | 65.6 | 53.5 |

TABLE 7-continued

| Bacteria/Compound retained by Seeds | Retaining Amount (/kg seeds) | Control Value | Estimated Value* |
|---|---|---|---|
| The Present Bacterial strain Ethaboxam | $1 \times 10^{10}$ cfu 0.15 g | 75.0 | 61.7 |
| The Present Bacterial strain Ethaboxam | $1 \times 10^{10}$ cfu 0.3 g | 84.4 | 67.2 |
| The Present Bacterial strain Metalaxyl | $1 \times 10^{10}$ cfu 0.01 g | 62.5 | 48.0 |
| The Present Bacterial strain Metalaxyl | $1 \times 10^{10}$ cfu 0.04 g | 75.0 | 56.3 |
| The Present Bacterial strain Metalaxyl | $1 \times 10^{10}$ cfu 0.16 g | 81.3 | 64.5 |
| The Present Bacterial strain Ethaboxam | $1 \times 10^{8}$ cfu 0.3 g | 81.3 | 66.0 |
| The Present Bacterial strain Metalaxyl | $1 \times 10^{6}$ cfu 0.01 g | 53.1 | 42.4 |
| The Present Bacterial strain Metalaxyl | $1 \times 10^{8}$ cfu 0.16 g | 78.1 | 63.2 |

*Control value estimated from the calculation by the Colby's equation

The compartment treated with the composition of the invention showed a synergistic controlling effect, for each combination of the present bacterial strain and the compound, compared with that of the corresponding compartment treated solely with the present bacterial strain or the compound.

Test Example 23

In a rotary seed treatment machine (trade name: HEGE11, manufactured by WINTERSTEIGER), soybean seeds (variety:"Hatayutaka") were treated by smearing treatment using a chemical liquid prepared by dissolving Tolclofos-methyl flowable formulation (42% flowable formulation, trade name: Rizolex, Valent U.S.A. Corporation), fludioxonil flowable formulation (20% flowable formulation, trade name: Savior flowable, Syngenta Japan) or the carboxamide compound (1) in acetone/Tween 20 (weight ratio=95:5) and diluting with water, and a flowable formulation of the present bacterial strain as obtained in Formulation Example 13, so that the soybean seeds retain the present bacterial strain and/or the compound in the amount shown in Table 8.

In a rotary seed treatment machine (trade name: HEGE11, manufactured by WINTERSTEIGER), soybean seeds thus treated with tolclofos-methyl, fludioxonil or the carboxamide compound (1) were treated with a flowable formulation of the present bacterial strain as obtained in Formulation Example 13, so that the soybean seeds retain the amount shown in Table 8.

A plastic pot was filled with a soil, and then, the soybean seeds, which have been treated with the present bacterial strain, compound or the present bacterial strain+compound as shown in Table 8, were seeded and covered with a soil, which has been mixed with damping-off fungus (*Rhizoctonia solani*) cultured in a bran medium. Cultivation was carried out in a greenhouse under irrigation ("treated compartment"). Also, similar procedures were conducted using untreated soybean seeds, instead of the treated soybean seeds, as described above for the treated compartment ("untreated compartment"). The plants were investigated 20 days after for the number of diseased plants, and the disease incidence was calculated by the following "Equation 1". The control value of the treated compartment was calculated by the following equation "Equation 2", based on the disease incidences of the treated compartment and the untreated compartment.

Disease incidence (%)=100×(number of diseased plant/total number of seeded seeds):  Equation 1

Control value (%)=100×[(disease incidence in untreated compartment disease incidence in treated compartment)/disease incidence in untreated compartment]:  Equation 2

TABLE 8

| Bacteria/Compound retained by Seeds | Retaining Amount (/kg seeds) | Control Value | Estimated Value* |
|---|---|---|---|
| The Present Bacterial strain | $1 \times 10^{10}$ cfu | 14.2 | — |
| The Present Bacterial strain | $1 \times 10^{6}$ cfu | 2.8 | — |
| The Present Bacterial strain | $1 \times 10^{7}$ cfu | 5.7 | — |
| The Present Bacterial strain | $1 \times 10^{11}$ cfu | 17.1 | — |
| Tolclofos-Methyl | 0.01 g | 11.4 | — |
| Tolclofos-Methyl | 0.05 g | 28.6 | — |
| Tolclofos-Methyl | 0.25 g | 42.8 | — |
| Fludioxonil | 0.004 g | 25.7 | — |
| Fludioxonil | 0.02 g | 37.1 | — |
| Fludioxonil | 0.1 g | 48.6 | — |
| The Carboxamide Compound (1) | 0.0004 g | 40.0 | — |
| The Carboxamide Compound (1) | 0.002 g | 54.3 | — |
| The Carboxamide Compound (1) | 0.01 g | 65.7 | — |
| The Present Bacterial strain Tolclofos-Methyl | $1 \times 10^{10}$ cfu 0.01 g | 31.4 | 24.0 |
| The Present Bacterial strain Tolclofos-Methyl | $1 \times 10^{10}$ cfu 0.05 g | 51.4 | 38.7 |
| The Present Bacterial strain Tolclofos-Methyl | $1 \times 10^{10}$ cfu 0.25 g | 68.6 | 50.9 |
| The Present Bacterial strain Fludioxonil | $1 \times 10^{10}$ cfu 0.004 g | 48.6 | 36.3 |
| The Present Bacterial strain Fludioxonil | $1 \times 10^{10}$ cfu 0.02 g | 62.8 | 46.1 |
| The Present Bacterial strain Fludioxonil | $1 \times 10^{10}$ cfu 0.1 g | 74.3 | 55.9 |
| The Present Bacterial strain The Carboxamide Compound (1) | $1 \times 10^{10}$ cfu 0.0004 g | 60.0 | 48.5 |
| The Present Bacterial strain The Carboxamide Compound (1) | $1 \times 10^{10}$ cfu 0.002 g | 77.1 | 60.8 |
| The Present Bacterial strain The Carboxamide Compound (1) | $1 \times 10^{10}$ cfu 0.01 g | 91.4 | 70.6 |
| The Present Bacterial strain Tolclofos-Methyl | $1 \times 10^{6}$ cfu 0.01 g | 17.1 | 13.9 |
| The Present Bacterial strain Tolclofos-Methyl | $1 \times 10^{7}$ cfu 0.05 g | 42.8 | 32.6 |
| The Present Bacterial strain Fludioxonil | $1 \times 10^{6}$ cfu 0.004 g | 37.1 | 27.8 |
| The Present Bacterial strain Fludioxonil | $1 \times 10^{7}$ cfu 0.02 g | 54.3 | 40.7 |
| The Present Bacterial strain Fludioxonil | $1 \times 10^{7}$ cfu 0.1 g | 62.8 | 51.5 |
| The Present Bacterial strain The Carboxamide Compound (1) | $1 \times 10^{11}$ cfu 0.0004 g | 62.8 | 50.3 |
| The Present Bacterial strain The Carboxamide Compound (1) | $1 \times 10^{6}$ cfu 0.01 g | 85.7 | 66.7 |

*Control value estimated from the calculation by the Colby's equation

The compartment treated with the composition of the invention showed a synergistic controlling effect, for each combination of the present bacterial strain and the compound, compared with that of the corresponding compartment treated solely with the present bacterial strain or the compound.

The invention claimed is:

1. A composition for control plant diseases comprising *Bacillus* strain APM-1 deposited under ATCC Accession No. PTA-4838 and one or more compounds selected from the group consisting of ethaboxam, tolclofos-methyl, metalaxyl, and fludioxonil,
wherein the composition comprises $10^{-5}$ to $10^{2}$ g of the compound per $10^{10}$ cfu of *Bacillus* strain APM-1.

2. A method for controlling plant diseases, comprising a step of applying the composition defined in claim 1 to a plant or a plant cultivation site.

3. The method for controlling plant diseases according to claim 2 wherein the plant is a genetically modified plant.

4. A plant seed or vegetative propagation organ comprising $10^{6}$ to $10^{13}$ cfu of *Bacillus* strain APM-1 and 0.0001 to 10 g of one or more compounds selected from the group consisting of ethaboxam, tolclofos-methyl, metalaxyl, and fludioxonil per 1 kg of the seed or vegetative propagation organ.

* * * * *